US008879745B2

(12) United States Patent
Anderson

(10) Patent No.: US 8,879,745 B2
(45) Date of Patent: Nov. 4, 2014

(54) METHOD OF DERIVING INDIVIDUALIZED GAIN COMPENSATION CURVES FOR HEARING AID FITTING

(75) Inventor: Dean Robert Gary Anderson, Orem, UT (US)

(73) Assignee: Dean Robert Gary Anderson as Trustee of the D/L Anderson Family Trust, Orem, UT (US)

( * ) Notice: Subject to any disclaimer, the term of this patent is extended or adjusted under 35 U.S.C. 154(b) by 946 days.

(21) Appl. No.: 12/901,301

(22) Filed: Oct. 8, 2010

(65) Prior Publication Data
US 2011/0075853 A1   Mar. 31, 2011

Related U.S. Application Data

(63) Continuation-in-part of application No. 12/508,441, filed on Jul. 23, 2009, and a continuation-in-part of application No. 12/861,486, filed on Aug. 23, 2010.

(60) Provisional application No. 61/249,939, filed on Oct. 8, 2009.

(51) Int. Cl.
*H04R 25/00*  (2006.01)
*A61B 5/00*   (2006.01)
*A61B 5/11*   (2006.01)
*A61B 5/12*   (2006.01)

(52) U.S. Cl.
CPC ............... *A61B 5/11* (2013.01); *H04R 2430/03* (2013.01); *A61B 5/12* (2013.01); *H04R 25/70* (2013.01); *H04R 25/40* (2013.01); *A61B 5/6814* (2013.01); *A61B 5/6803* (2013.01)
USPC .............................. 381/60; 381/23.1; 381/314

(58) Field of Classification Search
USPC ............. 381/60, 312, 313, 314, 315; 600/559
See application file for complete search history.

(56) References Cited

U.S. PATENT DOCUMENTS

| | | | |
|---|---|---|---|
| 5,197,332 | A | 3/1993 | Shennib |
| 5,325,436 | A | 6/1994 | Soli et al. |
| 5,396,560 | A | 3/1995 | Arcos |
| 5,717,767 | A | 2/1998 | Inanaga et al. |
| 5,825,894 | A | 10/1998 | Shennib |
| 5,868,682 | A | 2/1999 | Combs |
| 5,870,481 | A | 2/1999 | Dymond et al. |
| 5,878,146 | A | 3/1999 | Andersen |
| 5,923,764 | A | 7/1999 | Shennib |
| 6,167,138 | A | 12/2000 | Shennib |

(Continued)

FOREIGN PATENT DOCUMENTS

| | | |
|---|---|---|
| EP | 1933590 A1 | 6/2008 |
| GB | 2394632 A | 4/2004 |
| WO | 2008141672 A1 | 11/2008 |

*Primary Examiner* — Davetta W Goins
*Assistant Examiner* — Phylesha Dabney
(74) *Attorney, Agent, or Firm* — Morriss O'Bryant Compagni, PC

(57) ABSTRACT

A method of deriving individual gain compensation curves for hearing aid fitting includes providing a system that detects, measures and records head azimuth for sound direction affirmation by a patient and provides a plurality of audio signals through a plurality of test sequences to the ears of the patient, including establishing a comfortable listening level of the patient, establishing binaural balance for right and left ears, establishing loudness discomfort levels of the patient, establishing thresholds-of-hearing levels of the patient and generating a binaurally balanced measurement array of measured equal-loudness levels and measured thresholds-of-hearing levels for both left and right ears.

39 Claims, 19 Drawing Sheets

(56) References Cited

U.S. PATENT DOCUMENTS

| | | | |
|---|---|---|---|
| 6,201,875 B1 | 3/2001 | Davis et al. | |
| 6,236,731 B1 | 5/2001 | Brennan et al. | |
| 6,389,142 B1 | 5/2002 | Hagen et al. | |
| 6,567,524 B1 | 5/2003 | Svean | |
| 6,574,342 B1 | 6/2003 | Davis et al. | |
| 6,577,740 B1 | 6/2003 | Bordewijk | |
| 6,674,862 B1 | 1/2004 | Magilen | |
| 6,731,769 B1 | 5/2004 | Lenhardt | |
| 6,885,752 B1 | 4/2005 | Chabries et al. | |
| 6,912,289 B2 | 6/2005 | Vonlanthen et al. | |
| 7,058,188 B1 | 6/2006 | Allred | |
| 7,206,423 B1 * | 4/2007 | Feng et al. | 381/312 |
| 7,418,379 B2 | 8/2008 | Vierthaler | |
| 7,502,483 B2 | 3/2009 | Rikimaru | |
| 7,903,833 B2 | 3/2011 | Goldberg et al. | |
| 8,094,834 B1 | 1/2012 | Brungart | |
| 2003/0142746 A1 | 7/2003 | Tanaka et al. | |
| 2004/0006283 A1 | 1/2004 | Harrison et al. | |
| 2004/0076301 A1 | 4/2004 | Algazi et al. | |
| 2006/0008102 A1 | 1/2006 | Westergaard | |
| 2006/0182294 A1 | 8/2006 | Grasbon et al. | |
| 2006/0204013 A1 | 9/2006 | Hannibal et al. | |
| 2006/0210090 A1 | 9/2006 | Shennib | |
| 2007/0127753 A1 | 6/2007 | Feng et al. | |
| 2007/0223720 A1 | 9/2007 | Goldberg et al. | |
| 2009/0116657 A1 | 5/2009 | Edwards et al. | |
| 2011/0170711 A1 | 7/2011 | Rettelbach et al. | |

* cited by examiner

FIG. 15

METHOD OF DERIVING INDIVIDUALIZED GAIN COMPENSATION CURVES FOR HEARING AID FITTING

CROSS-REFERENCE TO RELATED APPLICATION

The present invention claims priority to U.S. patent application Ser. No. 12/861,486 filed on Aug. 23, 2010, U.S. patent application Ser. No. 12/508,441 filed on Jul. 23, 2009, and U.S. Provisional Patent Application Ser. No. 61/249,939 filed on Oct. 8, 2009, the entirety of each of which is incorporated by this reference.

BACKGROUND

1. Field of the Invention

The present invention relates to the derivation of individual gain compensation curves for digital hearing aids for binaural patients through the use of near instantaneous head azimuth detection and measurement for instinctual sound direction affirmation in the fitting process. More specifically, the present invention relates to basic data collection strategies and data collection flow diagrams for supplemental testing, to advanced data collection strategies and data collection flow diagrams for standalone testing, and gain compensation programming strategies.

2. State of the Art

Individuals with at least some hearing capacity can determine sound direction. When both ears are involved in this localization process (binaural hearing), sound direction is perceived by differences in both sound amplitude ("interaural amplitude difference") and slight timing variation ("interaural time difference") as well as audio diffraction for the ear that is closer to the sound source versus the shadowed ear. The process of sound localization also includes head movement to give affirmation of where the sound is coming from.

For individuals with normal hearing, the ability to perceive sound direction helps us to focus on a single conversation within a crowded and noisy room. Normal hearing individuals are typically able to converse (i.e., able to get 50% of words and 95% of sentences correct) at −5 dB signal-to-noise ("S/N") ratio in a noisy environment (e.g., 60 dB Sound Pressure Level ("dB$_{SPL}$")). Sound pressure is the local pressure deviation from the ambient (average, or equilibrium) pressure caused by a sound wave. The SI unit (International System of Units) for sound pressure is the Pascal (symbol: Pa). The instantaneous sound pressure is the deviation from the local ambient pressure $p_0$ caused by a sound wave at a given location and given instant in time. The effective sound pressure is the root mean square of the instantaneous sound pressure over a given interval of time (or space).

The sound pressure deviation (instantaneous acoustic pressure) p is:

$$p = \frac{F}{A}$$

where: F=force, A=area.

The entire pressure $p_{total}$ is:

$$p_{total} = p_0 + p$$

where: $p_0$=local ambient atmospheric (air) pressure, p=sound pressure deviation.

Sound pressure level (SPL) or sound level $L_p$ is a logarithmic measure of the rms sound pressure of a sound relative to a reference value. It is measured in decibels (dB) above a standard reference level.

$$L_p = 10\log_{10}\left(\frac{p_{rms}^2}{p_{ref}^2}\right) = 20\log_{10}\left(\frac{p_{rms}}{p_{ref}}\right) dB,$$

where: $p_{ref}$ is the reference sound pressure and $p_{rms}$ is the rms sound pressure being measured. The commonly used reference sound pressure in air is $p_{ref}$=20 μPa (rms), which is usually considered the threshold of human hearing (roughly the sound of a mosquito flying 3 m away).

Research has shown that the ear can also detect a time difference (i.e., delay) of sound of as little as 30 microseconds. For a typical adult-sized head, the time lag for sound waves travelling from one side of the head to the other is approximately 0.6 milliseconds. "Head shadow" refers to the attenuation and diffraction of sounds as they travel from one side of the head to the other. High frequency sounds are more affected by head shadow because of the shorter wavelength. The head shadow effect can be as much as 15 dB at 4000 Hz.

The "just noticeable difference" in azimuth perception for most normal hearing listeners when the sound source is straight ahead is a mere 1 degree. At lower frequency pulsed tones (i.e., below 1000 Hz) individuals with normal hearing have superior azimuth perception. Direction perception below 1000 Hz is predominantly a function of the person's ability to detect the slight timing variation that occurs between the left and right ears as the sound waves travel to the more distant ear. For higher continuous tone frequencies (i.e., between 1000 and 4000 Hz) a normal person can more easily detect changes in intensity. Sound direction localization for higher frequencies (between 1000 and 4000 Hz) is dominated by perception of differences in sound amplitude due to both an individual's frequency sensitivity and head shadow.

When sound comes from "off-angle" or to the side, the sound at each ear also "sounds" different. Sound to the furthest ear has to diffract (bend) around the head. Not only does the sound wave attenuate and arrive slightly later, but it is also altered in terms of the balance of high and low frequencies it contains (i.e., spectral alteration). Sounds with short wavelength (i.e., high frequency) do not diffract as well, so the furthest ear hears less of the high frequencies contained in the sound. The listener's brain detects this difference in frequency content, and uses the detected difference to locate the source of the sound. Head shadow diffraction also produces an overall diffraction modulation (i.e., interference patterns) for the shadowed ear.

In human speech, spoken vowels generate primarily low frequency sounds and spoken consonants generate primarily high frequency sounds. For an example, when the word "choose" is spoken, the "ch" and "z" sounds are formed by escaping air past the tongue, roof of the mouth, teeth and lips and have a rich high frequency spectrum (i.e., above 1000 Hz). These sounds are referred to as unvoiced sounds (e.g. fricatives, plosives). The "oo" sound is a voiced sound created by air motion sympathetic vibrations with the vocal cords and resonance within the lung/throat/mouth/nasal cavity and is typically below 1000 Hz. Thus, for speech recognition in the presence of ambient noise when aided by directional hearing or localization, the human binaural auditory system requires information perceived by differences in sound amplitude, slight timing variation and diffraction effects.

Head movement is also an important component of sound direction localization. The existence of ongoing spatial recalibration in the human auditory system and accuracy is steadily reacquired with changes over time. Additionally, interaural time and level differences are not the only means by which one identifies the location of a sound source. Head movement, which results in sound changes in frequency, intensity and timing between the left and right ears assist the auditory system to locate the sound source.

Typically, a person with hearing degradation in one or both ears can still perceive sound direction. The use of hearings aids, however, will often times diminish the ability to perceive sound direction. Improper hearing aid fitting can further diminish sound direction perception. This is an obvious disadvantage to the use of hearing aids. Most often, others must raise their voice when talking to someone with hearing aids to communicate in a noisy environment.

The inability to clearly understand speech in a noisy environment is the most frequently reported complaint of hearing-impaired people that use hearing aids. Moreover, as hearing loss progresses, individuals require greater and greater signal-to-noise ratios in order to understand speech. It has been universally accepted through digital signal processing research that signal processing alone will not improve the intelligibility of a signal in noise, especially in the case where the signal is one person talking and the noise is other people talking (i.e., "the cocktail party effect"). With currently available hearing aids, there is no way to communicate to the digital processor that the listener now wishes to turn his/her attention from one talker to another, thereby reversing the roles of signal and noise sources.

While significant advances have been made in the last decade in hearing aid technology to improve the ability to hear conversations in noisy environments, such advances were often the result of the elimination of certain defects in hearing aid processing, such as distortion, limited bandwidth, peaks in the frequency response and improper automatic gain control ("ACG") action. Research conducted in the 1970's, before these defects were corrected, indicated that the wearer of hearing aids typically experienced an additional deficit of 5 to 10 dB above the unaided condition in the S/N required to understand speech. Normal hearing individuals wearing the same hearing aids also experienced a 5 to 10 dB deficit in the S/N required to carry on a conversation, indicating that the hearing aids were at fault.

As a result of diminished sound localization ability and the S/N levels for individuals wearing hearing aids in a noisy environment, most hearing aid wearers try to avoid such situations or end up removing the hearing aids in order to regain the ability to focus on a particular conversation, despite the subsequent loss of understanding in portions of what is often perceived as muffled conversation. In order for hearing impaired individuals to be able to hear discrete conversations in a noisy environment, an increase in S/N is required, even when no defects in the hearing aid processing exist. Those with mild hearing loss typically need about 2 to 3 dB greater S/N than those with normal hearing. Those with moderate hearing loss typically need 5 to .7 dB greater S/N, and those with severe hearing loss typically need a 9 to 12 dB increase in S/N.

One attempt in the art to improve S/N in hearing aids is through the use of directional microphones. Because directional microphones are subject to the effects of back and/or side lobes, a deficiency in such hearing aids is a result of these effects in directional microphone sound reception. As a result, a person wearing hearing aids with directional microphones, sometimes ends up primarily hearing the conversation behind him/her through the back lobe of the directional microphone.

Another deficiency in the current state of hearing aids related to improving speech recognition in noisy environments is directly related to the current fitting protocols used to acoustically fit hearing aids to a hearing impaired individual. The current fitting process often results in substantial loss of localization perception for the user by making only a fraction of the speech cues available. In addition, the maximum loudness discomfort levels of the patient are not measured or accounted for in current hearing aid fitting protocols.

The basic signal processing architecture set forth in U.S. Pat. No. 6,885,752 to Chabries, et al. is representative of most modern hearing aids and uses multi-band, multiplicative compression. The band-pass filters typically generate nine or more fixed channels with band-pass resolutions spaced at half octaves or less between 200 Hz and 12,000 Hz.

In each frequency band, non-linear amplification or gain (referred to as multiplicative compression) is applied to each channel individually. As set forth in U.S. Pat. No. 6,885,752, one factor in restoring hearing for individuals with hearing losses is to provide the appropriate gain. For each frequency band where hearing has deviated from normal, a different multiplicative compression is supplied to make the greatest use of the individual's remaining hearing sensation. The multi-band, multiplicative AGC adaptive compression approach used in U.S. Pat. No. 6,885,752 and most modern hearing aids has no explicit feedback or feed forward.

Assessment of hearing is the first step in the prescribing and acoustic fitting of a hearing aid. Accurate assessment of the individual's hearing function is important because all hearing aid prescriptive formulas depend on one or more sets of hearing diagnostic data. Well known methods of acoustically fitting a hearing aid to an individual begin with the measurement of the threshold of the individual's hearing by using a calibrated sound-stimulus-producing device and calibrated headphones. The measurement of the threshold of hearing takes place in an isolated sound room. It is usually a room where there is very little audible noise. The sound-stimulus-producing device and the calibrated headphones used in the testing are typically referred to as an "audiometer."

Generally, the audiometer generates pure tones, warbled tones, swept tones or band-pass noise centered at various frequencies between 125 Hz and 12,000 Hz that are representative of the frequency bands or channels designed within the hearing aid. These tones are transmitted through the headphones of the audiometer to the individual being tested. The intensity or volume of each tone is varied until the individual can just barely detect the presence of the tone. For each tone, the intensity of the tone at which the individual can just barely detect the presence of the tone, is known as the individual's air conduction threshold of hearing. Although the threshold of hearing is only one element among several that characterizes an individual's hearing loss, it is the predominant measure traditionally used to acoustically fit a hearing compensation device.

The usable range of hearing (also called the dynamic range) is usually characterized along coordinates of frequency and sound pressure level and falls between an area bounded by the audibility curve (or threshold of hearing) and the Loudness Discomfort Level (LDL), which are sounds too loud to listen to in comfort or are unpleasant or are painful. Many hearing aid fitting protocols include the measurement of the Loudness Discomfort Level as a function of frequency.

Examples of more advanced protocols are set forth in U.S. Pat. Nos. 6,201,875 and 6,574,342. These patents disclose a system where curves are generated for a series of different loudness levels (or loudness contours) such as contours for: Uncomfortably Loud, Loud but OK, Comfortable but Slightly Loud, Comfortable, Comfortable but Slightly Soft, Soft, and Very Soft. Also disclosed is a system to dynamically change the non-linear gain for each frequency channel based on the family of curves.

Once the threshold of hearing in each frequency band has been determined, this threshold of hearing is used to estimate the amount of amplification, compression, and/or other adjustment that will be employed to compensate for the individual's loss of hearing. The implementation of the amplification, compression, and/or other adjustments and the hearing compensation achieved thereby depends upon the hearing compensation device being employed. There are various formulas known in the art which have been used to estimate the acoustic parameters based upon the observed threshold of hearing. These include industry hearing compensation device formulas known as NAL1, NAL2, and POGO. There are also various proprietary methods used by various hearing-aid manufacturers. Additionally, based upon the experience of the person performing the testing and the fitting of the hearing-aid to the individual, these various formulas may be adjusted. The appropriate gain calculated for each frequency channel may also include considerations and adjustments for the additional measurements of loudness discomfort level or other measured loudness contours. The appropriate gain calculated for each frequency channel then becomes the hearing compensation curve or look-up table data programmed into the hearing aid for each frequency channel. Programming the hearing aid memory for the hearing aid digital signal processor (DSP) may be done dynamically during the fitting process with devices such as the GN Otometrics HI-PRO programming interface so that changes to the hearing compensation curves or look-up table data may be evaluated immediately by the person being fitted and the audiologist.

Another condition associated with sensorineural hearing loss is loudness recruiting. Loudness recruitment is a condition that results in an abnormally-rapid increase in loudness perception with relatively small increases in sound levels above the hearing threshold of the hearing impaired person. Recruitment is a common characteristic of hearing loss that results from damage to the sensory cells of the cochlea, the most common type of sensory hearing loss. For example, a person with loudness recruitment may not be able to hear high frequency sounds below 50 $dB_{SPL}$, but may find any sounds above 80 $dB_{SPL}$ uncomfortable and even distorted. For such a hearing impaired individual, recruitment can mean a collapse of loudness tolerance and the feeling of distortion of loud sounds.

Recruitment is always a by-product of a sensorineural hearing loss. Recruitment is usually due to a reduction in neural elements associated with the inner ear hair cells. This phenomenon occurs because at some decibel level, the normal hair cells adjacent to the damaged hair cells (corresponding to the frequency of a hearing loss) are "recruited." At the decibel level at which these recruited hair cells are triggered, the perceived loudness quickly increases and often causes hearing discomfort.

A known test for recruitment is Alternate Binaural Loudness Balancing (ABLB). ABLB compares the relative loudness of a series of tones presented alternately to each ear. In practice the ABLB test is rarely performed by audiologist while fitting hearing aids because of the time it takes to perform such tests using current testing methods and devices and the lack of use of such test result data by current systems for hearing aid fitting.

As current methods of hearing aid fitting do not typically account for loudness recruitment, patients having such a condition are often fitted with hearing aids that become uncomfortable to wear because the dynamic range of hearing is so easily exceeded by the hearing aid. In such cases, the only option is for the patient to manually turn the volume down on the hearing aid, which universally reduces the amplification for all frequencies and across all sound levels.

The goal of any hearing aid is to amplify or otherwise process sounds so that they can be comfortably heard and understood. For larger degrees of hearing loss involving loudness recruitment where even everyday speech communication is difficult, amplification is required. Amplification that is sufficient to make sub-threshold sounds audible, however, will tend to make higher-level sounds uncomfortably loud. Often gain compression techniques are employed to compensate for this problem. It is commonly believed in the art; however, that even with the best methods of compression, it is inevitable that hearing-aid amplified sounds will be at least somewhat louder than they would be for a normal-hearing person for some input levels. In addition, because of the techniques employed in current hearing testing systems, it is also the case that the best amplification compression methods will not be properly configured for a given patient because the patient has not been properly tested in order to generate the correct gain curves for the hearing aids.

Current methods of hearing aid fitting employ the use of subjective listening methods and interpretation of the test results, which typically rely on verbal communications of sound perception relayed between the patient and an audiologist administering the test. Patients' ability to quantify perceived loudness of a tone also varies by individual, especially when current testing methods may supply tones to each ear at spaced apart intervals or between hearing tests that are often several seconds apart. As such, a major deficiency of most hearing aid fitting protocols is the inaccurate test results that are often attained that are used as the basis for a hearing aid fitting.

Indeed, when such verbal test methods are used, discrepancies of 10 dB or more are not uncommon and have been reported to be found in 36% of threshold of hearing measurements. A typical binaural fitting of digital hearing aids having 9 band-pass channels requires a minimum of 18 hearing threshold measurements. Based on the known error rate of 36%, it is the case that six or seven measurements in such a test are likely in error.

Another major disadvantage of measurements obtained using a traditional transducer is that results are not interchangeable with measurements taken with another transducer for a given individual.

Still another deficiency of current audiometers is found within the audiometer standards. (See Specification of Audiometers, ANSI-S3.6-1989, American 45 Standards National Institute, the entirety of which is incorporated by this reference). For example, in speech audiometry evaluation, the speech stimuli level is adjusted for one ear and speech noise level (or masking) is separately adjusted in the opposite ear. Bilateral, asymmetric hearing loss is far more prevalent than symmetrical loss. Asymmetric hearing loss requires different hearing compensation curves for each ear. Moreover, spectral group velocities can shift and distort based on frequency and amplitude weighting and amplification through the non-ideal hearing aid components (for example: damping via ferrofluids purposely designed into some receiver-speakers to reduce unintended oscillations).

Accordingly, it would be advantageous to provide hearing aids and a hearing aid fitting system and method that provide improved methods for derivation of patient specific gain compensation curves. It would be a further advantage to utilize additional data collected during the fitting process to improve gain compensation programming strategies. These and other advantages are provided by hearing aids and a hearing aid fitting system and methods according to the present invention set forth hereinafter that incorporate head azimuth detection during the fitting process.

SUMMARY OF THE INVENTION

Accordingly, the present invention includes systems and methods for generating data in order to derive patient specific gain compensation curves for proper digital hearing aid fitting. The systems and methods of the present invention generate and collect additional data during the hearing aid fitting process to be used to improve gain compensation programming strategies. The additional data collected in addition to data generated and collected in traditional threshold-of-hearing measurements may include:

1) Patient specific equal-loudness comfort contours to mitigate Stenger effects and necessary for recruitment gain compression.
2) Patient specific binaurally correlated directional balance measurements as a function of both frequency and SPL to overcome signal-to-noise overhead requirements for communication in a noisy environment (2 to 3 dB for mild loss; 5 to 7 dB for moderate loss; and, 9 to 12 dB for severe hearing loss).
3) Patient specific loudness discomfort levels for recruitment gain compression.

The present invention includes systems and methods that overcome the practical limitations that would otherwise inhibit or preclude additional data collection, such as:

1) Collecting additional data within a reasonable time period.
2) Limiting the testing time period to reduce eventual patient testing fatigue.

The use of near instantaneous head azimuth detection and measurement for instinctual sound direction affirmation in the hearing aid fitting process according to the present invention provides means and methods to significantly increase data collection within a specified testing time period. When used as an autonomous standalone protocol, this approach enables the collection of a significant number (e.g., 150) of meaningful measurements within a relatively short total test period (e.g., 18 minutes). When this approach is used as an autonomous supplement to traditional threshold-of-hearing protocols, a short test (e.g., 6 minutes) test provides a binaurally balanced equal-loudness contour at the patient's comfortable listening level.

All measurements and data collected therefrom using the systems and methods of the present invention are left-right coordinated so that any minor independent adjustments made for gain compensation curves for one ear are dependently reflected in adjustments for gain compensation curves made for the other ear. The coordinated measurement data is also applicable for monaural fittings of binaural patients that may be practical for 25% of all fittings.

The foregoing advantages and characterizing features will become apparent from the following description of certain illustrative embodiments of the invention. The above-described features and advantages of the present invention, as well as additional features and advantages, will be set forth or will become more fully apparent in the detailed description that follows and in the appended claims. The novel features which are considered characteristic of this invention are set forth in the attached claims. Furthermore, the features and advantages of the present invention may be learned by the practice of the invention, or will be obvious to one skilled in the art from the description, as set forth hereinafter.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 15 computer display screen displaying test results generated according to the principles of the present invention for a patient with moderate hearing loss.

DETAILED DESCRIPTION OF THE ILLUSTRATED EMBODIMENTS

Figure 1:
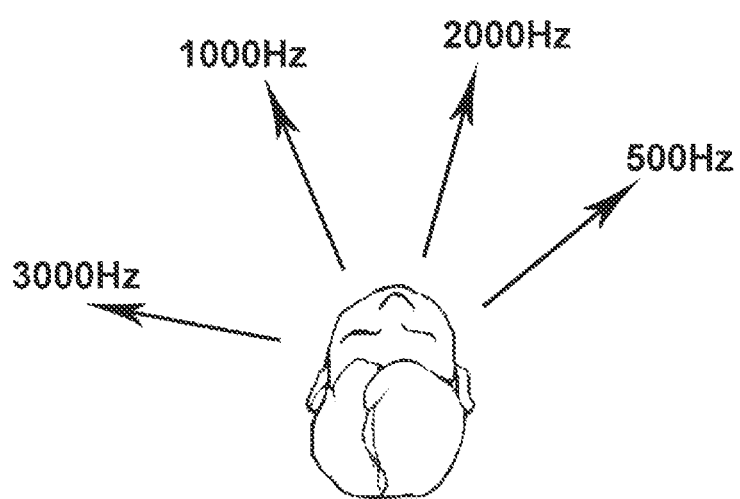
FIG. 1 is a top view of an individual experiencing uncorrelated binaural directional perception resulting from asymmetrical hearing loss and/or asymmetrical hearing aid acoustic fitting.

The following data collection strategies and dataflow diagrams show how . near instantaneous head azimuth detection and measurement for instinctual sound direction affirmation in the fitting process provides means and methods to significantly increase data collection within a specified testing time period. The strategies are provided in the context of a total test time target. FIG. 1 represents one individual's uncorrelated binaural directional perception resulting from asymmetrical hearing loss and/or asymmetrical hearing aid acoustic fitting. This is a primary cause for the increased signal-to-noise overhead requirement for the hearing impaired for correct sentence understanding in a noisy environment. The uncorrelated binaural direction perception is a function of both frequency and SPL.

Figure 2:
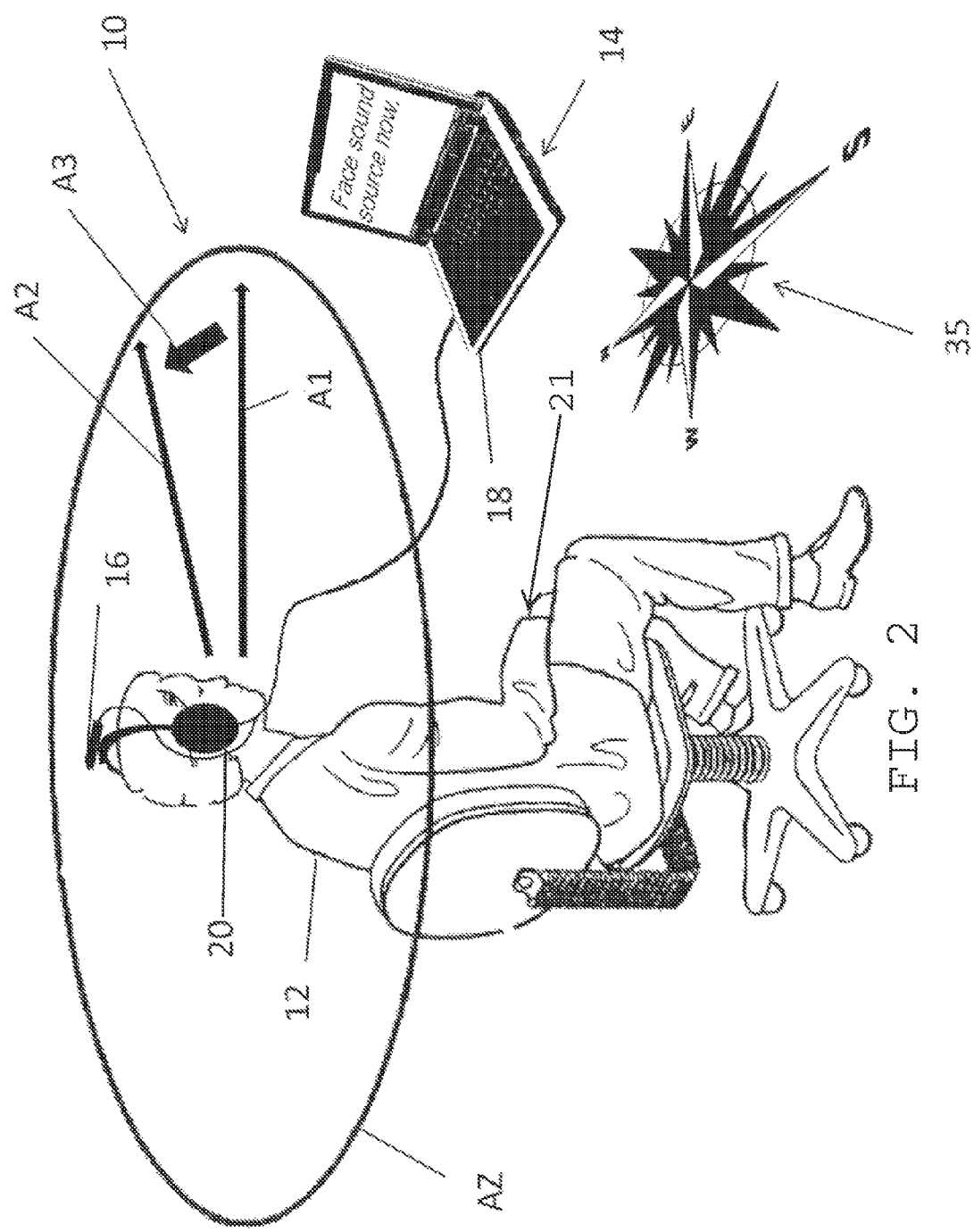
FIG. 2 is a side perspective view of a hearing aid fitting system and a subject person using the system in accordance with the principles of the present invention.

FIG. 2 illustrates a hearing aid fitting system, generally indicated at 10 in accordance with the principles of the present invention. An assessment of sound direction perception of an individual 12 is accurately made across a broad dynamic range in multiple frequency bands. Unlike prior art fitting systems, the tones presented to the individual 12 in the hearing loss assessment and fitting system 10 of the present invention are generated by an audiometer 14, which includes a head azimuth detecting device 16 that is measured in near real time by a computer 18, such as a personal computer, or other processing device that also provides corresponding binaural feedback and affirmation to the individual being fitted via a pair of headphones 20. A fixed purpose testing device (not shown) could also be used. The present hearing aid fitting system 10 coordinates directional perception sameness between the multiple frequency bands and across the wide dynamic range of the fitted hearing aids to improve speech understanding in noisy environments.

According to the present invention, the fitting system 10 transmits an audible tone through the headphones 20 in order to cause the individual 12 to localize the source of the tone. The tone is in stereo such that the tone will have a different intensity, delay (for pulsed tones) and/or phase, depending on the current head azimuth position, as illustrated by arrow A1, in each ear. The arrow A1 represents the individual's current head azimuth during the localization process as the individual searches for the sound source. The second arrow A2 represents the individual's final localization determination. The third arrow A3 represents the head azimuth error as measured in the search process. While the azimuth plane is represented by ring AZ, the system may only have the individual search within a 30 to 45 degree arc for all generated tones. Because the localization perception of most individuals is rather precise, it is not necessary to require the individual 12 to search for tones over a larger azimuth range. The compass rose 35 represents the local magnetic field.

The individual or patient 12 is also given a wireless mouse 21 to hold (not visible). The wireless mouse 21, or other patient input device, held by the patient 12 contains a mouse wheel, or other input mechanism to allow the patient 12 to provide input to the system 10. The mouse cursor position is clipped (or confined) during testing so that cursor pointing is not required for patient input responsibilities.

To optimize data collection, an autonomous protocol includes:
1) Patient test taking training.
2) Prioritization of testing and data collecting tasks.
3) Insurance of test data accuracy.
4) Optimization of the total test time to meet testing time targets.
5) Minimization of patient testing stress.

The patient interface is autonomous and uses a minimal patient proactive interface for the fitting system 10. It is possible to reduce the patient's testing input responsibilities to simply pressing a start button, using the mouse wheel for volume control, and head and/or chair movement in the azimuth plane. Even with this limited patient interface, however, autonomous test taking training is required.

As a general note, the audio signals presented within the test sequence set forth herein may comprise speech, pure continuous tones, and pulsing tones. Narrow-band noise, warbled tones, or other audio signals may also be used. It is important that the proper interrelated conversions for sound energy, sound pressure level, sound intensity and psychoacoustic perception are used when combining such diverse stimuli into a single test sequence.

According to the present invention, basic data collection strategies begin with initial patient instruction and adjustment of the patient comfort level. The patient is first shown an audio/visual demonstration that illustrates to the patient how to turn the mouse wheel to change the comfortable volume. The audio may use both male and female voices and may include low level background noise or music approximately 30 dB below the voice SPL. The audio continues to loop until the patient actually turns the mouse wheel. The audio portion of the loop serves to instruct the patient and also serves as the calibrated speech stimulus used to establish the comfortable listening level of the patient. Once the wheel stops turning and after an additional period of time (e.g., 7 seconds), the system presumes that the comfortable listening level of the patient has been established and the test continues on to the head movement portion of the training.

Head movement training also uses an interactive audio/visual loop. The user is prompted to turn his/her head to the right. Azimuth measurements are made and the loop is repeated as required until the sensor measures sufficient right movement. The same test is repeated for left movement.

The head movement training may be combined and used in conjunction with a lower intensity 1000 Hz continuous tone approximately 30 dB below the voice SPL. The tone, verbal instructions, and azimuth sensor are coordinated to realize sound localization and yield directional affirmation with head motion. The software can instruct the user to exaggerate head movement to insure that the user has sensed significant sound localization and directional affirmation. The audio/visual can repeat or refine these directions by looping or using more specific audio/visual instructions. Continuous measurements of the azimuth sensor 16 can be used to ensure the patient 12 is making the appropriate head movements and that the training has been understood by the correct completion of the training tasks. This test is conducted at the comfortable listening level.

In order to give the patient 12 the opportunity to get a feel for the testing procedure before the test actually begins, the system 10 is configured to provide a brief period of localization practice. This practice ensures test accuracy once the actual test begins. During the practice session, the patient 12 is instructed to practice precise localization with a 1000 Hz tone. The patient 12 is instructed to turn his/her head until the tone is balanced in both ears or until he/she feels that he/she is facing the sound source. Head movement is monitored during the process. The test continues until the average azimuth position and corresponding SPL for each ear for the last one second of data is essentially equal to the 2 preceding 1 second averages. For example, if the last 3 one second SPLs readings for the left ear are separated by no more than 0.4 dB and if the last 3 one second SPLs readings for the right ear are separated by no more than 0.4 dB, then the patient has concluded the azimuth head search and the average of averages for the right ear and the average of averages for the left ear are recorded as the binaural balance measurements. This process nulls potential palsy motion and sensor noise. This process will also null when head searching motions are balanced as in situations where the patient 12 is repeatedly shifting from one ear to the other to determine equal binaural balance.

Figure 3:
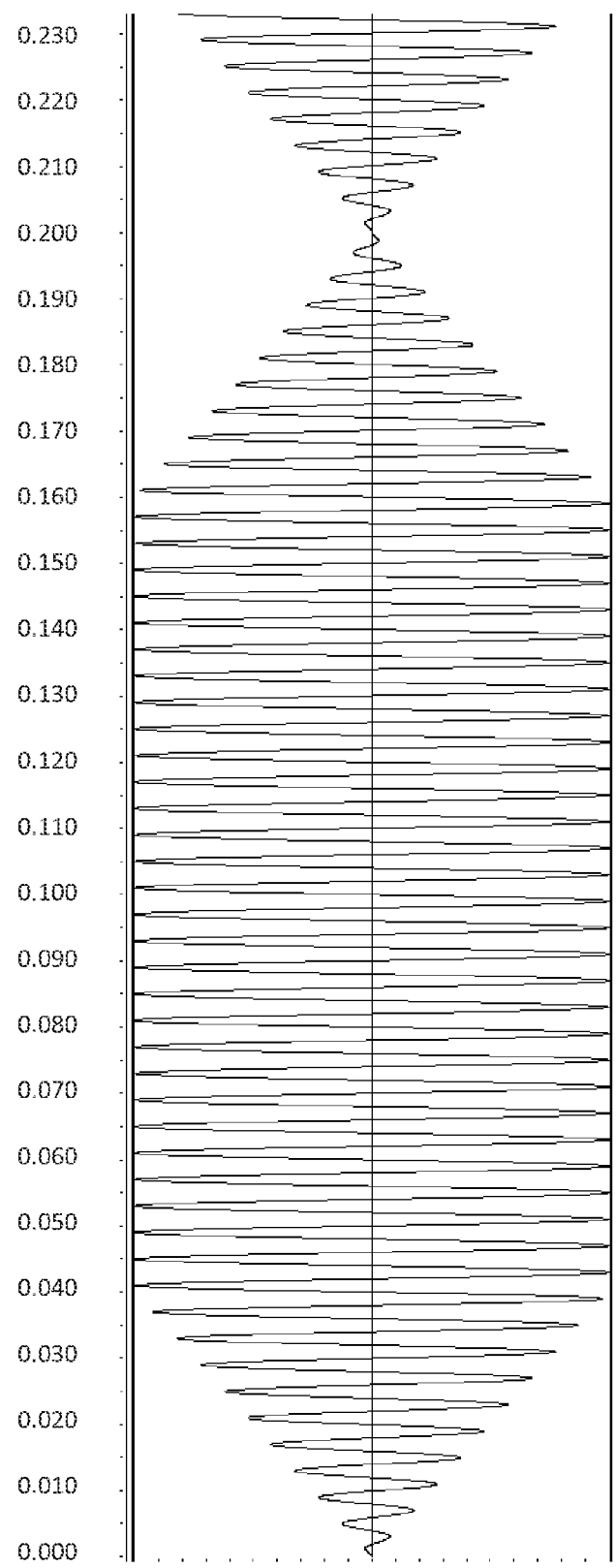
FIG. 3 is a graphical representation of modulated tone amplitude according to the principles of the present invention.

Although continuous tones, warble tones, narrow-band noise, etc. are most commonly used in this test, it has been found important for testing accuracy that there is compensation for the effects of listener fatigue. Each of the ears receiving the tone will eventually tire if the tone is simply continuous. One solution for this is to modulate the amplitude of the tone supplied to both ears. FIG. 3 is an example of such modulation. In this example, the tone is 250 Hz. The scale is in seconds. The tone has a 0.04 second fade-in and a 0.04 second fade-out which are repeated every 0.20 seconds. This results in a pulsing modulation which is repeating 300 times per minute. Other modulation rates, fade-ins and fade-outs may also be used. Modulations repeating 100 times per second are less stressful but generally produce less accurate results. When compensating for listener fatigue with pulsing modulation, the SPLs used and measured must be adjusted for the effect of the pulsing modulations.

Another audio/visual display informs the patient that the test will be repeated. The test is repeated until the patient can localize to essentially the same binaural balance level when using random simulated sound source locations. For example, if the last 2 localizations using random source locations are within 0.2 dB for each ear, the software presumes that the patient 12 has learned the localization process. Because this is an instinctual process, typically only 3 practice tests may be required to ensure test accuracy.

On average, the autonomous test sequence attempts to provide instructions, adjust the comfort level, and insure test accuracy within a 1 minute time allocation. The program for the first minute of patient testing is illustrated in the flow diagram illustrated in FIG. 4 and FIG. 5.

Figure 4:
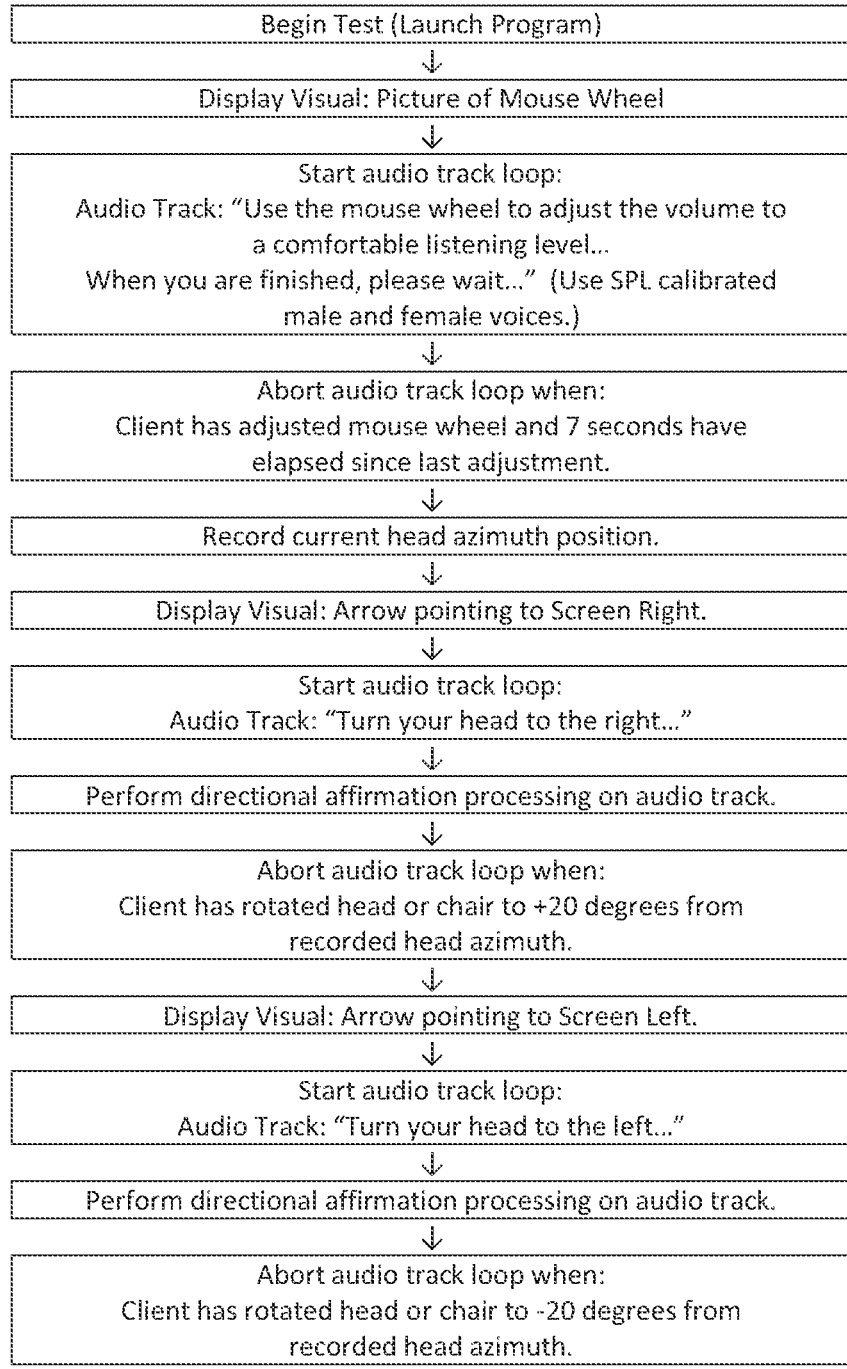
FIG. 4 is a schematic flow diagram of a hearing aid fitting test according to the principles of the present invention.

As illustrated in FIG. 4, the test is started by launching the program on the computer 18 or other testing system provided with the testing program according to the present invention. The visual display then shows a picture of a mouse wheel. An audio track loop is started. The audio track may provide the following instructions: "Use the mouse wheel to adjust the volume to a comfortable listening level . . . When you are finished, please wait . . . " (SPL calibrated male and female voices may be used.). The audio track is aborted when the client has adjusted the mouse wheel and 7 seconds have elapsed since last adjustment. The system then records current head azimuth position. The visual display shows an arrow pointing to the right side of the screen. An audio track is then started which states, "Turn your head to the right . . . " The system then performs directional affirmation processing on the audio track. The audio track loop is aborted when the client has rotated their head or chair to +20 degrees from recorded head azimuth. An arrow pointing to the left of the screen is then visually displayed and the audio track loop states, "Turn your head to the left . . . " The system then performs directional affirmation processing on the audio track and aborts the audio track loop when the client has rotated their head or chair to −20 degrees from recorded head azimuth.

Figure 5:
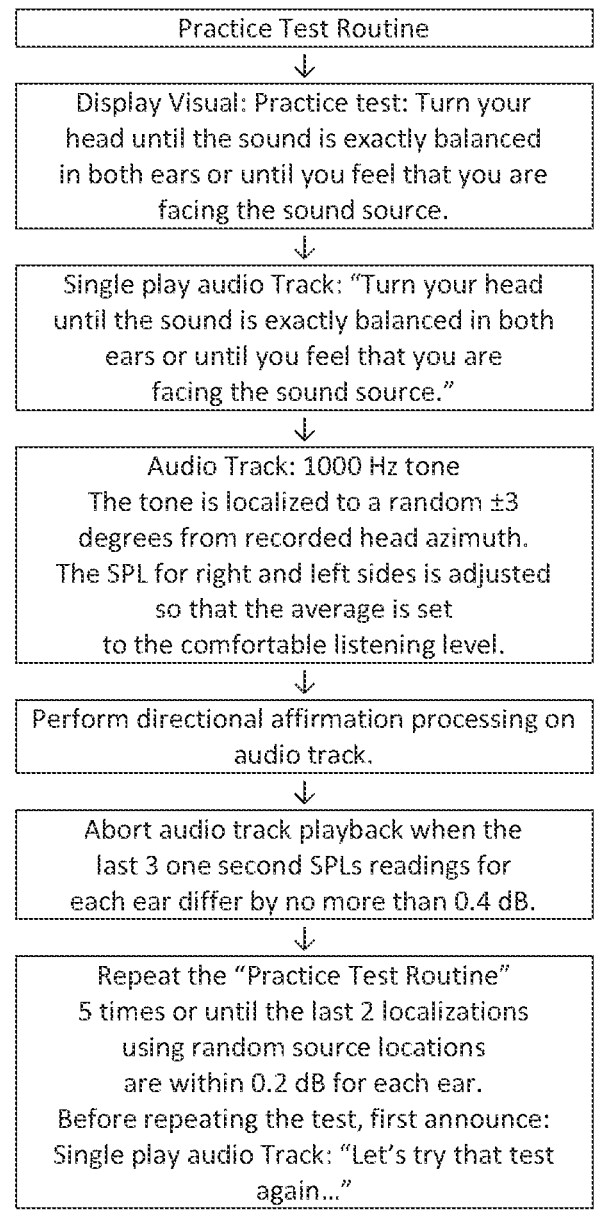
FIG. 5 is a schematic flow diagram of a practice hearing aid fitting test according to the principles of the present invention.

As illustrated in FIG. 5, a practice test routine according to the present invention includes the steps of displaying for the client a practice test with instructions to the client to "Turn your head until the sound is exactly balanced in both ears or until you feel that you are facing the sound source." A single play audio track then instructs the client to "Turn your head until the sound is exactly balanced in both ears or until you feel that you are facing the sound source." A 1000 Hz tone is generated. The tone is localized to a random ±3 degrees from recorded head azimuth. The SPL for right and left sides is adjusted so that the average is set to the comfortable listening level. The system then performs directional affirmation processing on audio track. The audio track is aborted when the last 3 one second SPLs readings for each ear differ by no more than 0.4 dB. The practice routine may be repeated 5 times or until the last 2 localizations using random source locations are within 0.2 dB for each ear. Before the test is repeated, the system announces via a single play audio track: "Let's try that test again . . . "

The next phase of the test is configured to provide binaurally balanced equal-loudness contours. Test data must be collected in order of priority. The most important and essential additional data is the comfortable listening level. The comfortable listening level is essential to adjust the speech volume for other test taking instructions and to determine the binaurally balanced equal-loudness contour. Employing the methods and systems of the present invention, only approximately 5 minutes are required to obtain a binaurally balanced equal-loudness contour. It is recommended that this contour be taken first at the comfortable listening level especially if the total test time window is restricted to 6 minutes (instruction time+contour test time).

If threshold-of-hearing measurements have been previously determined with other test protocol, this threshold data may be used to accelerate testing by avoiding tests at frequencies outside the patient's perceptional range. If this data has not yet been determined, it is strongly suggested that it be determined before this portion of the testing sequence to avoid testing at frequencies outside the patient's perceptional range. As will be discussed in more detail herein, advanced data collection strategies are provided for threshold testing.

Figure 6:
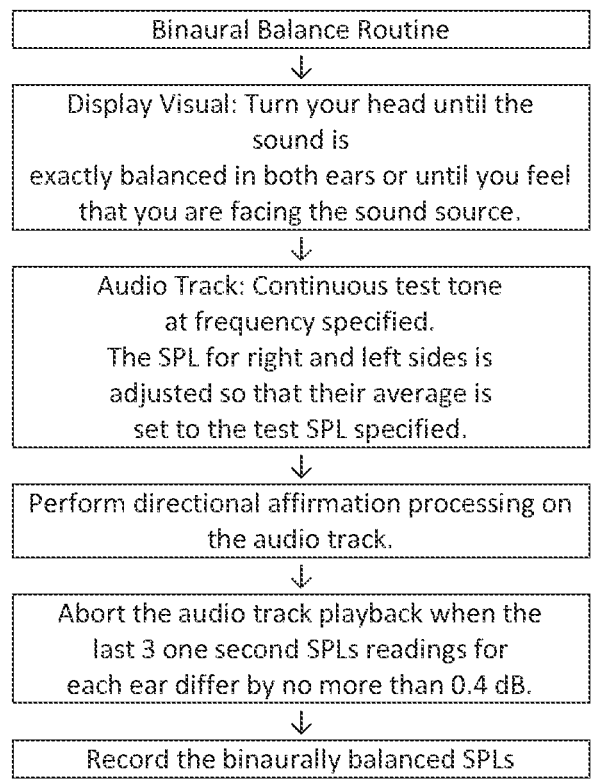
FIG. 6 is a schematic flow diagram of a binaural balance routine according to the principles of the present invention.

The system of the present invention further provides a binaural balance routine as illustrated in FIG. 6. If the binaurally balanced equal-loudness contour is to be performed at the comfortable listening level, the binaural balance levels derived during the above "Practice Test Routine" may be used. Otherwise, the first step is to establish the precise binaural balance at 1000 Hz and at SPLs for right and left sides where the average of the left and right is set to an alternate comfort setting (e.g. Loud, Slightly Loud, Slightly Soft, Soft, etc.). The binaural balance routine illustrated in FIG. 6 comprises the steps of prompting a visual display with instructions to the patient to "Turn your head until the sound is exactly balanced in both ears or until you feel that you are facing the sound source. An audio track is queued to produce a continuous test tone at a specified frequency. The SPL for right and left sides is adjusted so that the average of the two is set to the test SPL specified. Directional affirmation processing on the audio track is then performed. The audio track playback is aborted when the last 3 one second SPLs readings for each ear differ by a relatively small amount (e.g., no more than 0.4 dB). The binaurally balanced SPLs are then recorded by the system.

The binaural balance routine is set forth in generalized terms because it is used throughout the testing sequence. The testing sequence set forth in FIG. 6 is used for all binaural balance tests.

Figure 7:
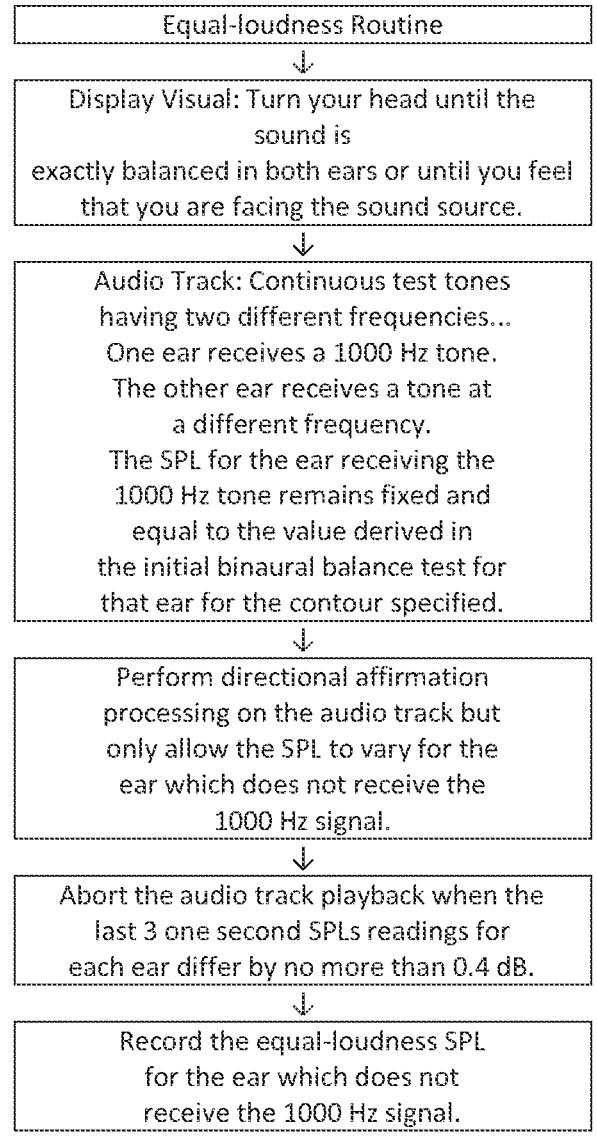
FIG. 7 is a schematic flow diagram of an equal-loudness routine according to the principles of the present invention.

As illustrated in FIG. 7, a different type of stimulus and a different routine are used to measure the equal-loudness levels which will be the basis for deriving the comfort contours. The steps set forth in the flow chart of FIG. 7 are used for all equal-loudness tests. By definition, two sine waves, of differing frequencies, are said to have equal-loudness levels if they appear equally loud to the patient. A 1000 Hz stimulus is applied to one ear. The other ear receives a stimulus at a different frequency. The SPL for the ear receiving the 1000 Hz signal is not allowed to vary. The other ear which is receiving stimulus at a different frequency has an SPL which varies according to azimuth head motion. The user is told to turn his/her head until the sound is exactly balanced in both ears.

As specifically set forth in FIG. 7, the equal-loudness routine comprises the steps of prompting the visual display to instruct the client to "Turn your head until the sound is exactly balanced in both ears or until you feel that you are facing the sound source." An audio track is queued and sent through the headphones being worn by the client that provide to the client continuous test tones having two different frequencies. One ear receives a 1000 Hz tone while the other ear receives a tone at a different frequency. The SPL for the ear receiving the 1000 Hz tone remains fixed and equal to the value derived in the initial binaural balance test for that ear for the contour specified.

The system then performs directional affirmation processing on the audio track but only allows the SPL to vary for the ear that does not receive the 1000 Hz signal. The audio track is aborted when the last 3 one second SPLs readings for each ear differ by a relatively small amount (e.g., no more than 0.4 dB). The system then records the equal-loudness SPL for the ear which does not receive the 1000 Hz signal.

To obtain an equal-loudness comfort contour, the routine is repeated for each frequency combination of the test sequence and for both ears. It is important to note that the SPL used for the ear receiving the fixed 1000 Hz signal is to be the value derived in the initial 1000 Hz binaural balance test for that ear.

Figure 8:
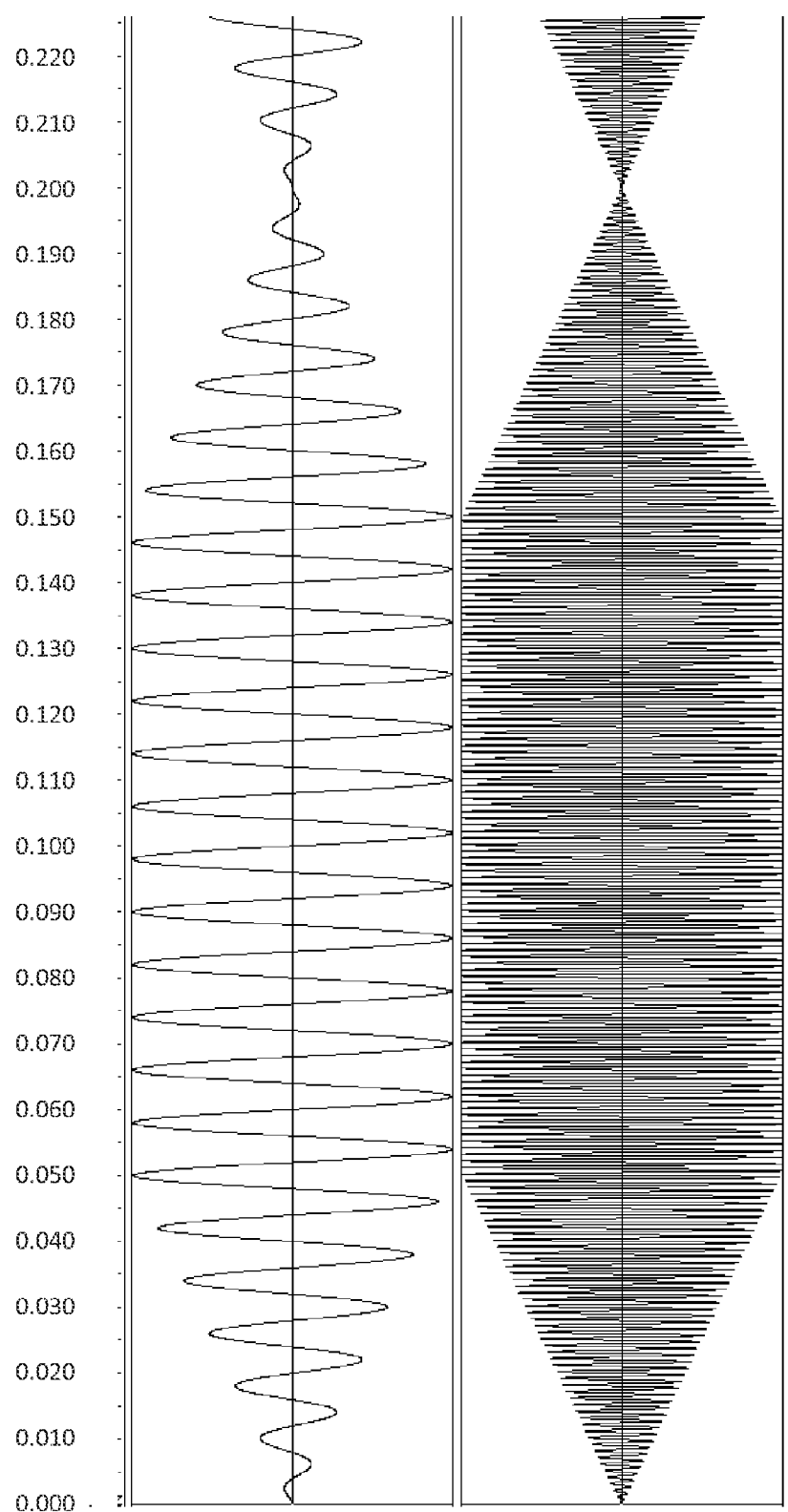
FIG. 8 is a graphical representation of modulated tone amplitudes supplied to both ears according to the principles of the present invention.

Again, it is also important to compensate for the effects of listener fatigue. The ear receiving a fixed 1000 Hz at a fixed SPL will eventually tire if the tone is not alternated between each ear for each test. It is desirable that continuous tones are used to reduce testing time. Another solution for listening fatigue, which unfortunately increases the overall testing time, is to modulate the amplitudes of both tones supplied to both ears. FIG. 8 is an example of such modulation. Two different frequencies are shown. The frequency shown on top is 125 Hz. The bottom frequency is 1000 Hz. The scale is in seconds. In this example, both tones use a 0.05 second fade-in and a 0.05 second fade-out which are repeated every 0.20 seconds. This results in a pulsing modulation which is repeating 300 times per minute. A modulation repeating 80 to 110 times per minute may also be used because it is more comfortable for the patient, however lower modulation frequencies result in reduced repeatability. When compensating for listener fatigue with pulsing modulation, the SPLs used and measured must be adjusted for the effect of the pulsing modulations.

Figure 9A:
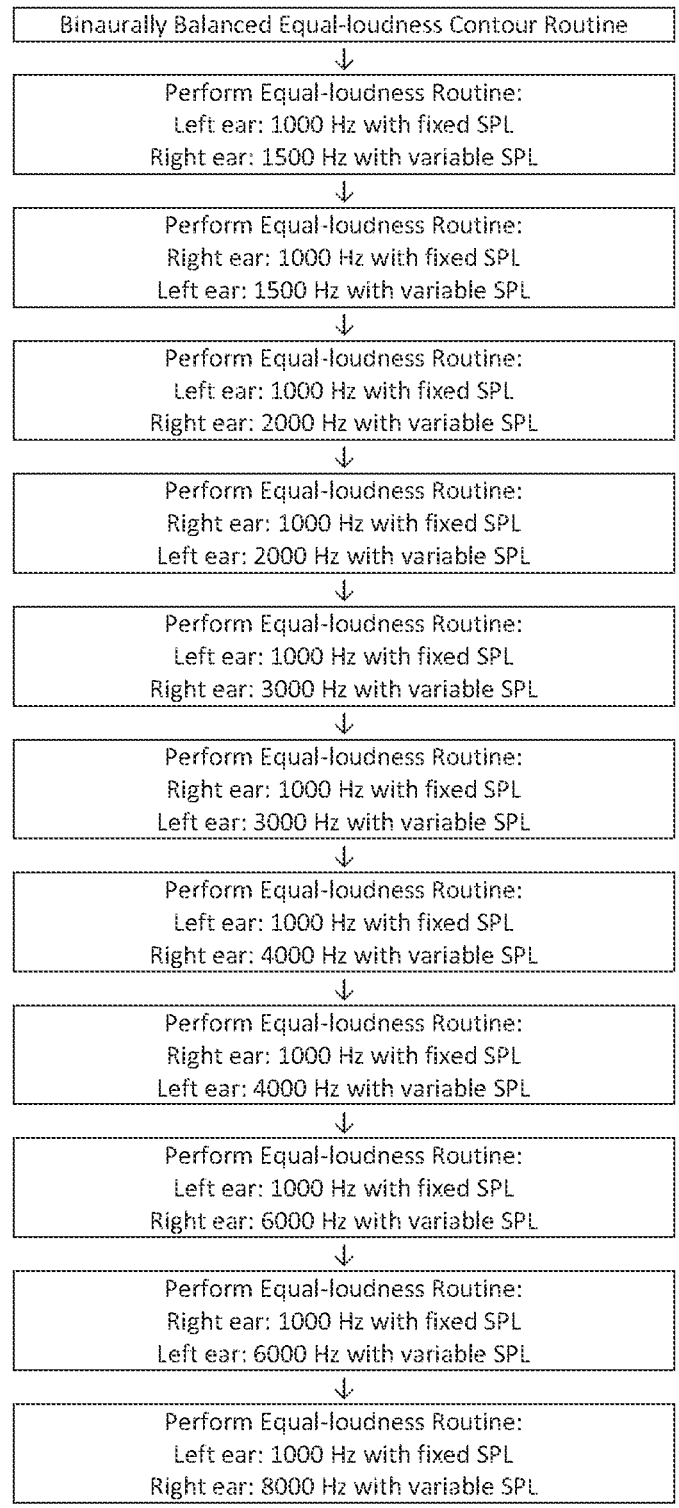
FIG. 9A is a schematic flow diagram of a binaurally balanced equal-loudness contour routine according to the principles of the present invention.
Figure 9B:
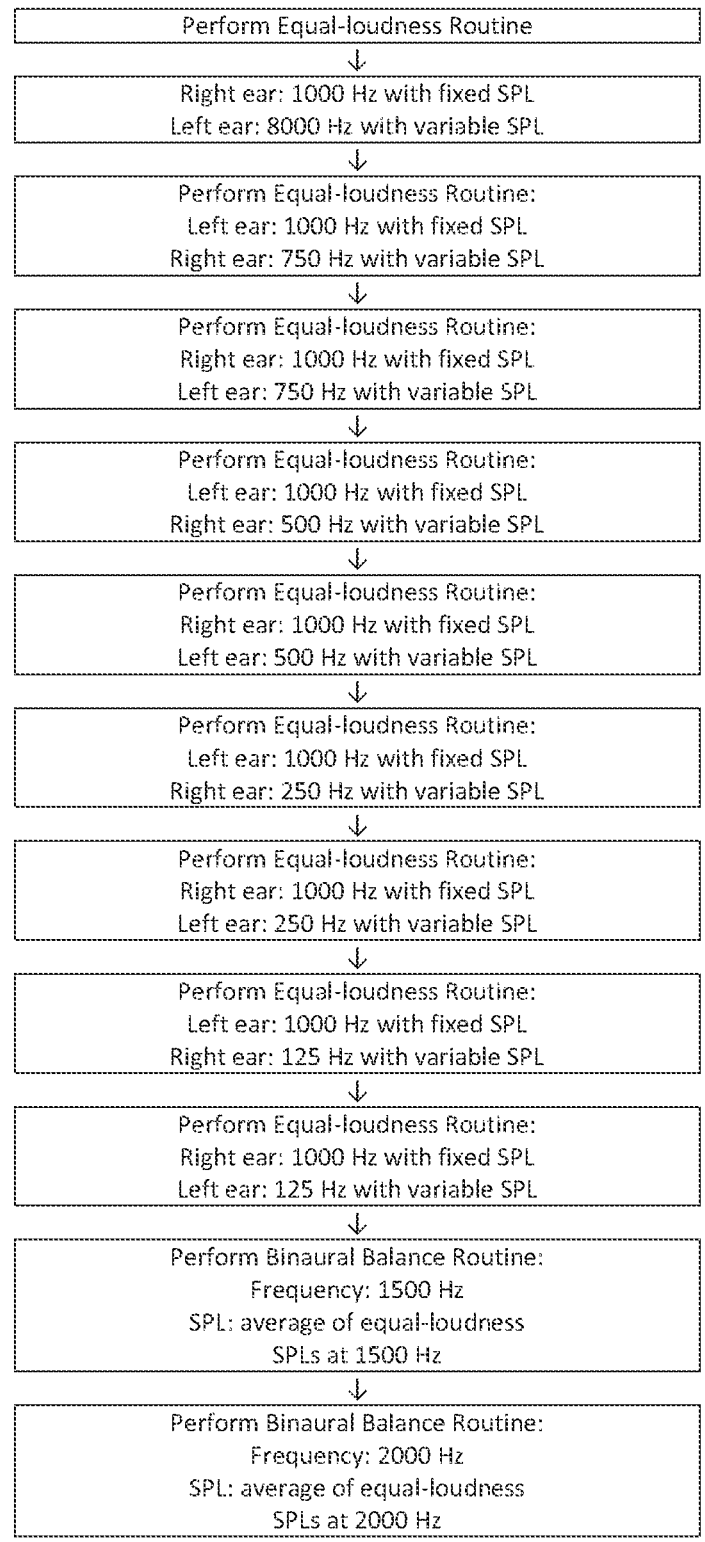
FIG. 9B is a schematic flow diagram of an equal-loudness routine according to the principles of the present invention.
Figure 9C:
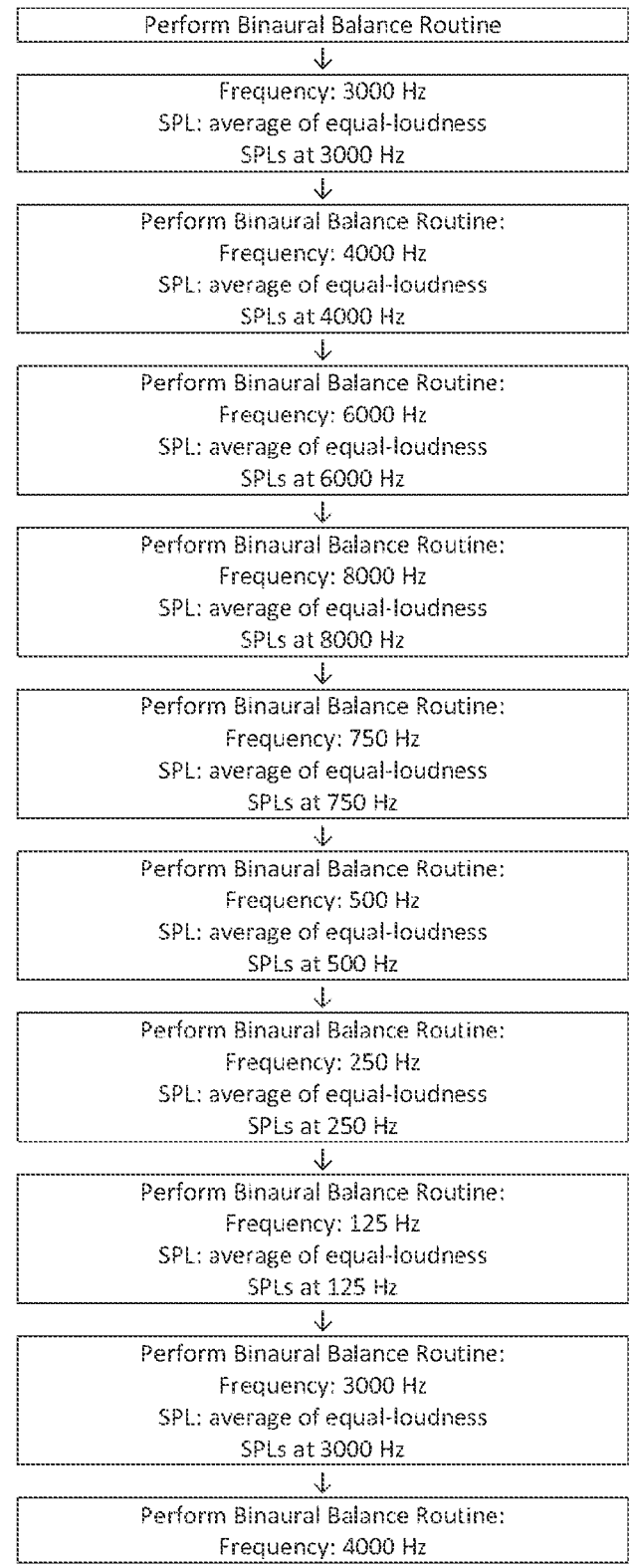
FIG. 9C is a schematic flow diagram of a binaural balance routine according to the principles of the present invention.

The binaurally balanced equal-loudness contour is derived using the routines as defined herein. The flow charts set forth in FIGS. 9A, 9B and 9C are used for all binaurally balanced equal-loudness contours. The frequencies cover the limited range: 125 Hz to 8000 Hz; which are the most important for clear understanding of speech. When the frequencies specified in this flowchart are outside the patient's perceptional range, the step is skipped. When the binaurally balanced equal-loudness contour routine is employed, the following steps are employed:

Perform Equal-loudness Routine with the left ear receiving a tone at 1000 Hz with fixed SPL and the right ear receiving a tone at 1500 Hz with variable SPL.

Perform Equal-loudness Routine with the right ear receiving a tone at 1000 Hz with fixed SPL and the left ear receiving a tone at 1500 Hz with variable SPL. The equal-loudness routine is subsequently repeated with the left and right ear tonal frequencies being varied as follows:

Left ear: 1000 Hz with fixed SPL; Right ear: 2000 Hz with variable SPL

Right ear: 1000 Hz with fixed SPL; Left ear: 2000 Hz with variable SPL

Left ear: 1000 Hz with fixed SPL; Right ear: 3000 Hz with variable SPL

Right ear: 1000 Hz with fixed SPL; Left ear: 3000 Hz with variable SPL

Left ear: 1000 Hz with fixed SPL; Right ear: 4000 Hz with variable SPL

Right ear: 1000 Hz with fixed SPL; Left ear: 4000 Hz with variable SPL

Left ear: 1000 Hz with fixed SPL; Right ear: 6000 Hz with variable SPL

Right ear: 1000 Hz with fixed SPL; Left ear: 6000 Hz with variable SPL

Left ear: 1000 Hz with fixed SPL; Right ear: 8000 Hz with variable SPL

Right ear: 1000 Hz with fixed SPL; Left ear: 8000 Hz with variable SPL

Left ear: 1000 Hz with fixed SPL; Right ear: 750 Hz with variable SPL

Right ear: 1000 Hz with fixed SPL; Left ear: 750 Hz with variable SPL

Left ear: 1000 Hz with fixed SPL; Right ear: 500 Hz with variable SPL

Right ear: 1000 Hz with fixed SPL; Left ear: 500 Hz with variable SPL

Left ear: 1000 Hz with fixed SPL; Right ear: 250 Hz with variable SPL

Right ear: 1000 Hz with fixed SPL; Left ear: 250 Hz with variable SPL

Left ear: 1000 Hz with fixed SPL; Right ear: 125 Hz with variable SPL

Right ear: 1000 Hz with fixed SPL; Left ear: 125 Hz with variable SPL

Subsequently, the binaural balance routine is performed in which the frequency of the tone is initially set at 1500 Hz with the SPL at the average of equal-loudness SPLs at 1500 Hz. The binaural balance routine is then repeated at various frequencies and SPLs as follows:

Frequency: 2000 Hz; SPL: average of equal-loudness; SPLs at 2000 Hz

Frequency: 3000 Hz; SPL: average of equal-loudness; SPLs at 3000 Hz

Frequency: 4000 Hz; SPL: average of equal-loudness; SPLs at 4000 Hz

Frequency: 6000 Hz; SPL: average of equal-loudness; SPLs at 6000 Hz

Frequency: 8000 Hz; SPL: average of equal-loudness; SPLs at 8000 Hz

Frequency: 750 Hz; SPL: average of equal-loudness; SPLs at 750 Hz

Frequency: 500 Hz; SPL: average of equal-loudness SPLs at 500 Hz

Frequency: 250 Hz; SPL: average of equal-loudness; SPLs at 250 Hz

Frequency: 125 Hz; SPL: average of equal-loudness; SPLs at 125 Hz

Frequency: 3000 Hz; SPL: average of equal-loudness; SPLs at 3000 Hz

Frequency: 4000 Hz

The basic testing strategy set forth above may be limited to an approximate 6 minute testing window and is therefore designed to be supplemental to traditional protocols which predetermine the patient's range of frequency perception for these tests. For more detailed testing and hearing aid fitting, the following advanced data collection strategies provide either advanced supplemental or stand-alone testing strategies using head azimuth measurement for instinctual sound direction affirmation in the fitting process. These advanced strategies include the determination of the patient's range of frequency perception.

The advanced strategies also begin with the same instructions and patient input given in the "Initial Instructions and Adjusting the Comfort Level" and in the "Localization Practice ensuring Test Accuracy". These instructions and comfort level determination may require approximately 1 minute of testing time.

At this point, the advanced strategies deviate in order to determine threshold-of-hearing and loudness discomfort levels (LDLs).

The methodology set forth herein determines loudness discomfort levels (LDLs) and thresholds of hearing with intensity sweeping methods where the patient is asked to press a mouse button or other user input device, such as a hand-held button, toggle or switch, when the stimulus becomes uncomfortably loud or is no longer perceptible.

Approximately 2 minutes are required to measure LDLs. Continuous tones are used. Each frequency for each ear is individually swept with ever increasing intensity. The patient clicks the mouse button or other user input device when the volume becomes uncomfortably loud. This method of autonomous swept continuous tones is repeatable within a few dB.

Approximately 3 minutes are required to measure the thresholds-of-hearing using the sweeping method. Pulsing tones are used as has been described above. Each frequency for each ear is individually swept with ever decreasing intensity. The patient clicks the mouse button or other user input device when the stimulus is no longer heard. Pulsing tones are easier for the patient to track as intensity diminishes because the pulsing is easily discerned until perception disappears. This approach will yield a slightly different result than the traditional "method of limits" protocol. Swept pulsing tones are advantageous however because they are consistently repeatable within 1 or 2 dB.

Together these autonomous methods for determining thresholds and LDLs are very repeatable and add only 5 minutes to the total test time. Training may first required to instruct the patient on how to click a mouse button or activate another user input device in order to make the LDL and threshold measurements.

Figure 10:
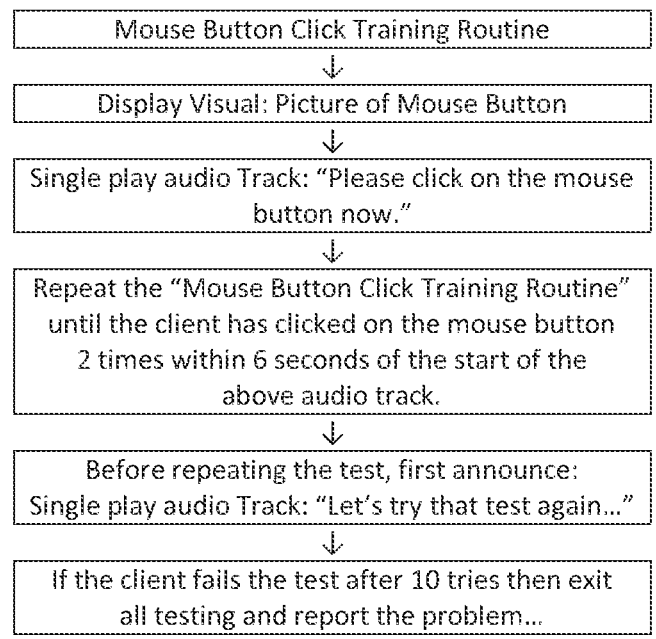
FIG. 10 is a schematic flow diagram of a mouse button click training routine according to the principles of the present invention.

As illustrated in FIG. 10, the patient is provided with instructions for clicking a mouse button in response to certain test cues. The flow chart parallels the training instructions given previously and should be performed by most users in 18 seconds or less. When the mouse button click training routine is initiated, the visual display shows a picture of the mouse and mouse button. An audio track plays and states, "Please click on the mouse button now." The mouse button click training routine is repeated until the client has clicked on the mouse button 2 times within 6 seconds of the start of the audio track. Before the test is repeated, an audio track is played that states, "Let's try that test again . . . " If the client fails the test after a predetermined number of attempts, (e.g., 10 tries) then the program is exited, all testing is terminated and a problem is reported.

Figure 11:
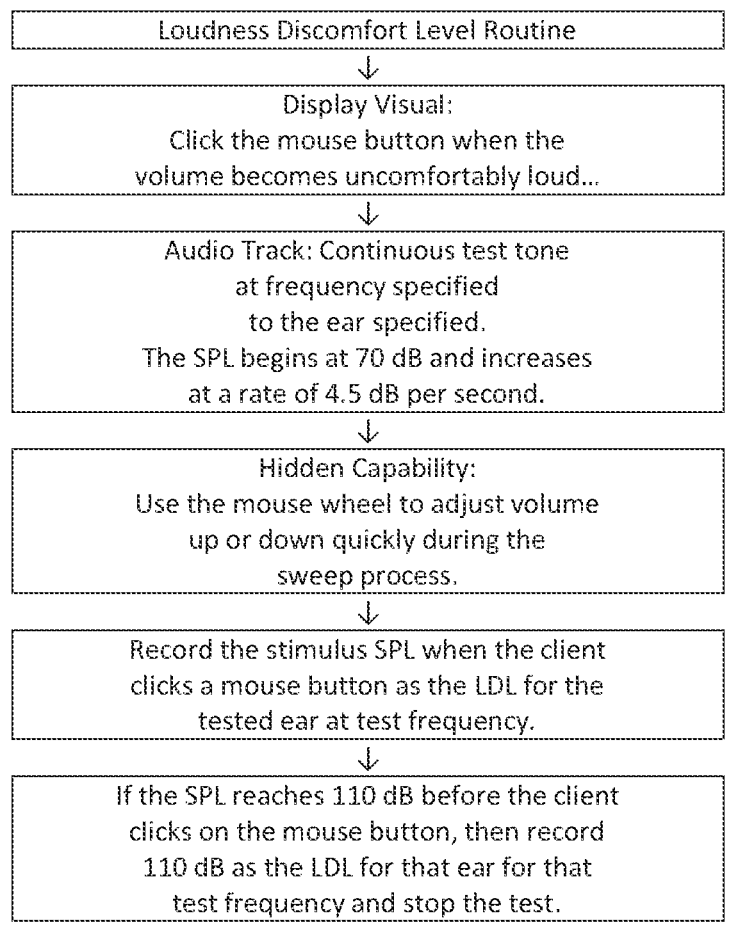
FIG. 11 is a schematic flow diagram of a loudness discomfort level routine according to the principles of the present invention.

As further illustrated in FIG. 11, each frequency for each ear is individually swept with ever increasing intensity in order to determine the LDL of the patient. A comfortable rate to increase the sound intensity is 4.5 dB per second. The SPL for the sweep can start at 70 dB. The stimulus used consists of a continuous tone at the frequency specified. The flow chart describes the routine for the general case when testing one frequency applied to one ear and is used for all LDL tests. The loudness discomfort level routine starts by displaying a prompt to the client that sates, "Click the mouse button when the volume becomes uncomfortably loud." An audio track is then played that constitutes a continuous test tone at a specified frequency and to a specified ear. The SPL begins at 70 dB and increases at a rate of 4.5 dB per second.

The loudness discomfort level routine may include a hidden capability in which the mouse wheel, or other user input device, is used to adjust volume up or down quickly during the sweep process. The system then records the stimulus SPL when the client clicks the mouse button as the LDL for the tested ear at test frequency. If the SPL reaches 110 dB before the client clicks on the mouse button, then the system records 110 as the LDL for that ear for that test frequency and stops the test.

Figure 12A:
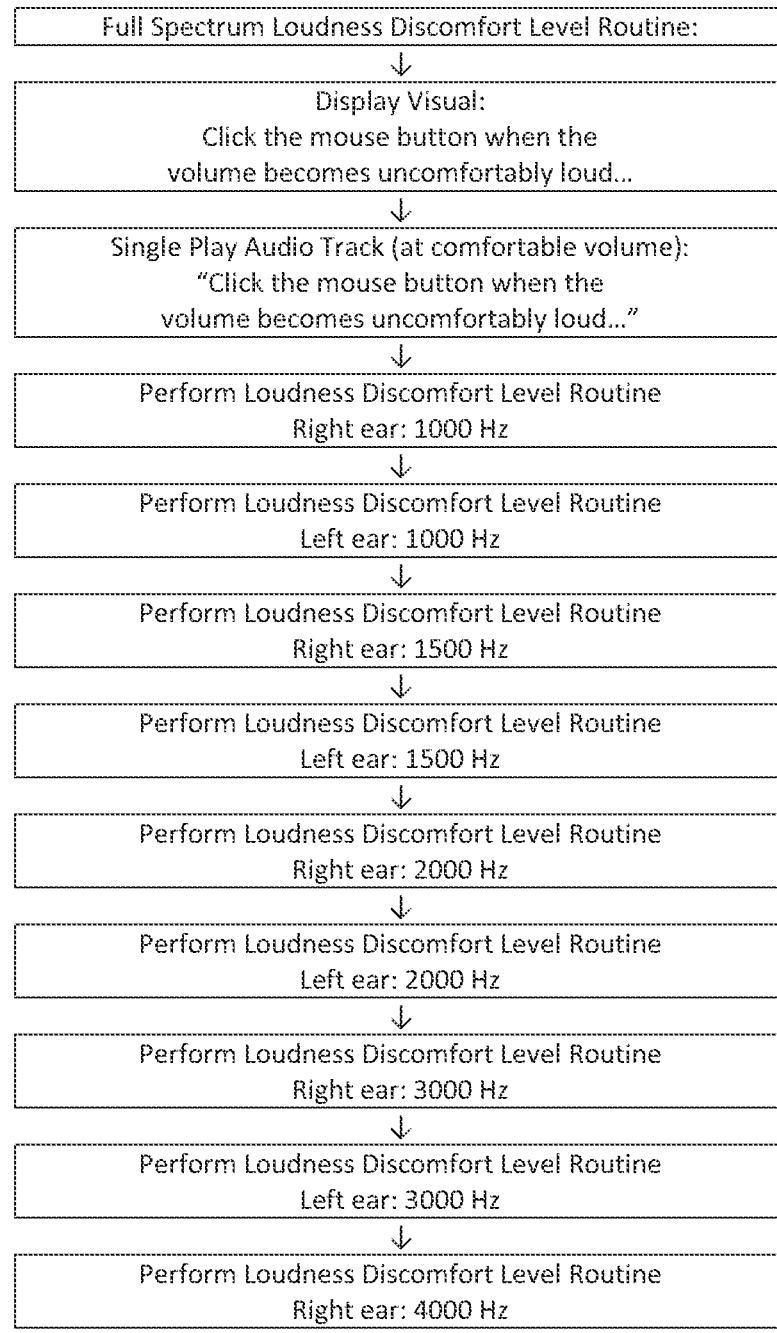
FIGS. 12A and 12B are schematic flow diagrams of a full spectrum loudness discomfort level routine according to the principles of the present invention.
Figure 12B:
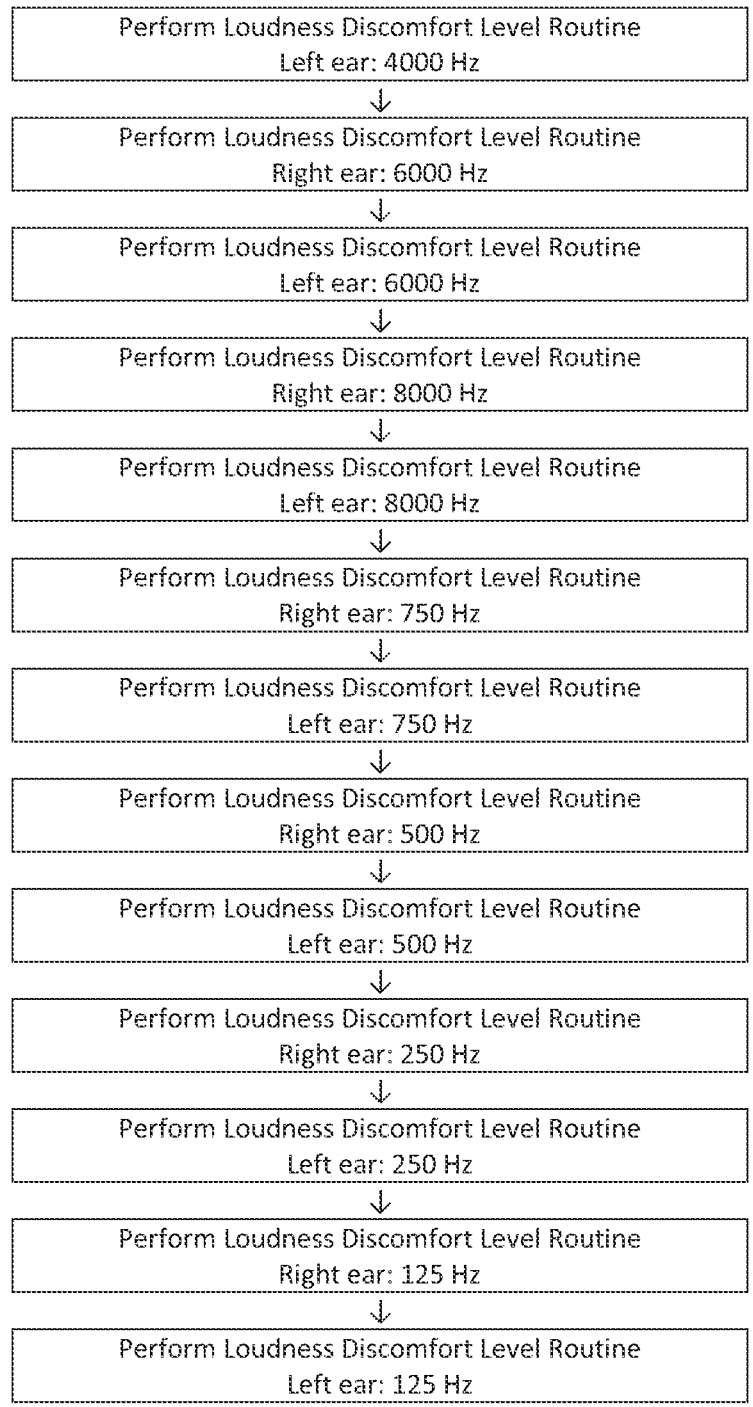

As shown in FIGS. 12A and 12B, a "full spectrum" LDL Routine is derived using the Loudness Discomfort Level routine set forth in FIG. 11. For full spectrum LDL, the frequencies cover the limited range: 125 Hz to 8000 Hz; which are the most important for clear understanding of speech. Testing is alternated between each ear to reduce listening fatigue.

Figure 13:
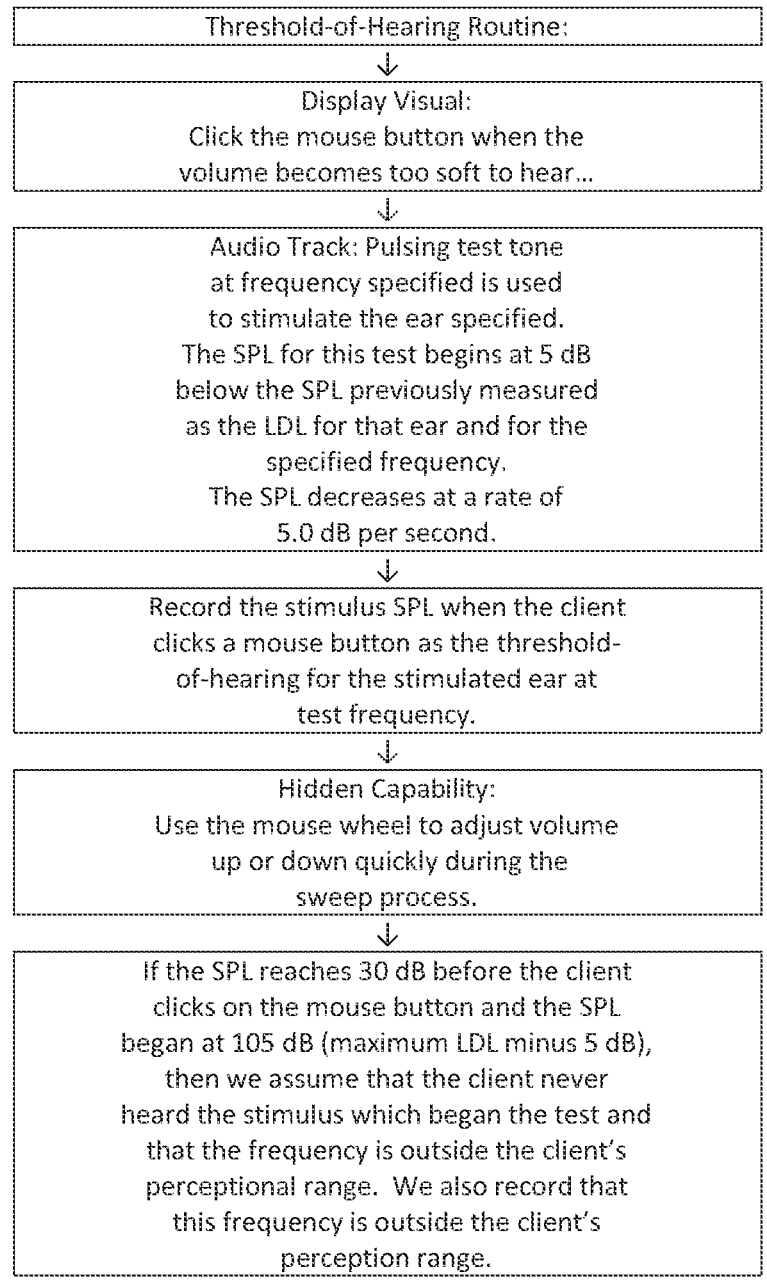
FIG. 13 is a schematic flow diagram of a threshold-of hearing routine according to the principles of the present invention.

Accordingly, a full spectrum loudness discomfort level routine as set forth in FIGS. 12A and 12B starts with a visual display of instructions to the client to "Click the mouse button when the volume becomes uncomfortably loud." A single play audio track (at comfortable volume) is started with instructions to "Click the mouse button when the volume becomes uncomfortably loud." The program then initiates a plurality of loudness discomfort level routines for each ear and at various frequencies as follows:

Right ear: 1000 Hz
Left ear: 1000 Hz
Right ear: 1500 Hz
Left ear: 1500 Hz
Right ear: 2000 Hz
Left ear: 2000 Hz
Right ear: 3000 Hz
Left ear: 3000 Hz
Right ear: 4000 Hz
Left ear: 4000 Hz
Right ear: 6000 Hz
Left ear: 6000 Hz
Right ear: 8000 Hz
Left ear: 8000 Hz
Right ear: 750 Hz
Left ear: 750 Hz
Right ear: 500 Hz
Left ear: 500 Hz
Right ear: 250 Hz
Left ear: 250 Hz
Right ear: 125 Hz
Left ear: 125 Hz FIG. 13 illustrates a method for determining the threshold-of-hearing. Each frequency for each ear is individually swept with ever decreasing intensity. A comfortable rate to decrease the sound intensity is, for example, 5.0 dB per second. The SPL for the sweep can start at 5 dB below the LDL for the tested ear at the tested frequency. The stimulus used consists of a pulsing tone as described above at the frequency specified. The flow diagram of FIG. 13 illustrates a routine for the general case for testing one frequency applied to one ear and is then used for all threshold-of-hearing tests. The threshold-of-hearing routine starts by displaying instructions to the client such as "Click the mouse button when the volume becomes too soft to hear." An audio track produces a pulsing test tone at frequency specified to stimulate the ear specified according to the testing protocol. The SPL for this test begins at 5 dB below the SPL previously measured as the LDL for that ear and for the specified frequency. The SPL decreases at a rate of 5.0 dB per second. The system records the stimulus SPL when the client clicks a mouse button as the threshold-of-hearing for the stimulated ear at test frequency. The routine may include a hidden capability to use the mouse wheel to adjust volume up or down quickly during the sweep process. If the SPL reaches 30 dB before the client clicks on the mouse button and the SPL began at 105 dB (maximum LDL minus 5 dB), then the program assumes that the client never heard the initial stimulus tone that began the test and that the specific frequency produced is outside the client's perceptional hearing range. The system also records that this frequency is outside the client's hearing perception range.

Figure 14A:
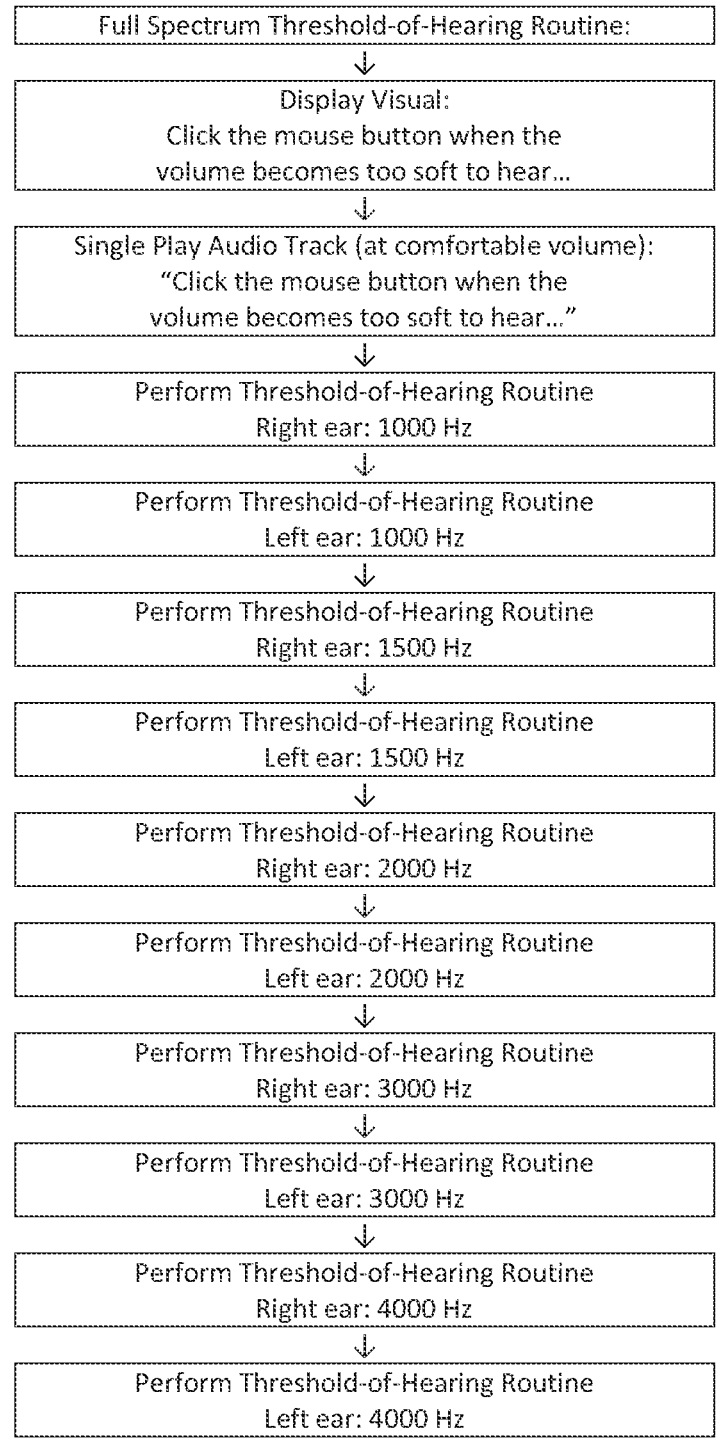
FIGS. 14A and 14B are schematic flow diagrams of a full spectrum threshold-of hearing routine according to the principles of the present invention.
Figure 14B:

As further illustrated in FIGS. 14A and 14B, a "full spectrum" threshold-of-hearing routine is derived using the threshold-of-hearing routine defined above. The method includes using frequencies covering the limited range of 125 Hz to 8000 Hz; which are the most important frequencies for clear understanding of speech. Testing is alternated between each ear to reduce listening fatigue. Thus, a full spectrum threshold-of-hearing routine will include providing instructions to the client on a visual display to "Click the mouse button when the volume becomes too soft to hear." A single play audio track (at comfortable volume) instructs the client to "Click the mouse button when the volume becomes too soft to hear." The program then executes a number of threshold-of hearing subroutines as follows.

Right ear: 1000 Hz
Left ear: 1000 Hz
Right ear: 1500 Hz
Left ear: 1500 Hz
Right ear: 2000 Hz
Left ear: 2000 Hz
Right ear: 3000 Hz
Left ear: 3000 Hz
Right ear: 4000 Hz
Left ear: 4000 Hz
Right ear: 6000 Hz
Left ear: 6000 Hz
Right ear: 8000 Hz
Left ear: 8000 Hz
Right ear: 750 Hz
Left ear: 750 Hz
Right ear: 500 Hz
Left ear: 500 Hz
Right ear: 250 Hz
Left ear: 250 Hz
Right ear: 125 Hz
Left ear: 125 Hz The advanced data collection procedures described with reference to FIGS. 10-14B, should only take approximately 6.3 minutes to complete, with the following individual test protocol approximate times:

1 minute—Initial Instructions and Adjusting the Comfortable Listening Level (see FIG. 4).

0.3 minutes—Instructions for Clicking a Mouse Button (see FIG. 10)

2 minutes—Full Spectrum Loudness Discomfort Level Routine (see FIG. 11).

3 minutes—Full Spectrum Threshold-of-Hearing Routine (see FIG. 12).

At this point, the advanced strategy resumes with a binaurally balanced equal-loudness contour routine given at the comfortable listening level.

5 minutes—Binaurally Balanced Equal-loudness Contour Routine given at the Comfortable Listening Level (see FIG. 9).

The test time at this point is approximately 11.3 minutes.

The advanced data collection procedure concludes with the derivation of an array of binaurally balanced measurements.

A patient with moderate hearing loss will typically take another 7 minutes to complete the tests for a binaurally balanced measurement array. Thus, the total testing time for the advanced strategy will be approximately: 11.3 minutes +7 minutes=18.3 minutes.

The Binaural Balance Routine set forth in FIG. 6 is employed for the remaining pairs of measurements in the array. The array is bounded by the predetermined LDLs and Thresholds-of-Hearing values. The array includes the binaurally balanced equal-loudness contour at the comfortable listening level. Additional binaurally balanced measurements are made and included for the frequencies: 125 Hz; 250 Hz; 500 Hz; 750 Hz; 1000 Hz; 1500 Hz; 2000 Hz; 3000 Hz; 4000 Hz; 6000 Hz; and, 8000 Hz. If any of these frequencies is outside the patient's range of perception for either ear, these frequencies are excluded from the remaining measurements.

The Binaural Balance Routine is used for each frequency and for SPLs beginning 10 dB below the equal-loudness levels and repeated for each 10 dB below that until the intended measurement would be below either threshold-of-hearing right or left levels for that frequency. At least one pair of binaural balance measurements should be made between the comfortable listening level and the thresholds-of-hearing. The 10 dB requirement should be reduced if needed to allow at least one pair of binaural balance measurements in this range.

The Binaural Balance Routine is also used for each frequency and for SPL beginning 7 dB above the equal-loudness levels and repeated for each 7 dB above that until the intended measurement would exceed either loudness discomfort level for that frequency. At least one pair of binaural balance measurements should be made between the comfortable listening level and the LDL. The 7 dB requirement should be reduced if needed to allow at least one pair of binaural balance measurements in this range.

The following Table 1 is representative of a binaural balance measurement array for a patient at one frequency within his/her range of frequency perception according to the above sequence of measurements.

TABLE 1

| Binaurally Balanced Measurement Array: | SPL Left Ear | SPL Right Ear | Measurement Level: |
|---|---|---|---|
| Monaurally Measured: | | | |
| Loudness Discomfort Level: | 91.8 dB | 88.7 dB | |
| Binaural Balance: | 87.2 dB | 82.4 dB | Average $SPL_{CLL}$ + 7 dB |
| Binaurally Balanced | | | |
| Equal-loudness Level: | 79.3 dB | 76.3 dB | Average $SPL_{CLL}$ |

TABLE 1-continued

| Binaurally Balanced Measurement Array: | SPL Left Ear | SPL Right Ear | Measurement Level: |
|---|---|---|---|
| Binaural Balance: | 69.2 dB | 66.4 dB | Average $SPL_{CLL}$ − 10 dB |
| Binaural Balance: | 58.5 dB | 57.1 dB | Average $SPL_{CLL}$ − 20 dB |
| Binaural Balance: Monaurally Measured: | 48.2 dB | 47.4 dB | Average $SPL_{CLL}$ − 30 dB |
| Threshold-of-Hearing Level: | 43.1 dB | 32.7 dB | |

The Average $SPL_{CLL}$ is the numerical average of the left ear SPL and right ear SPL measurements at the Comfortable Listening Level (plus or minus the amount indicated in Table 1 as applicable).

In the testing strategies described, LDLs and Thresholds-of-Hearing for each frequency are obtained monaurally. Binaurally balancing of these measurements may certainly be performed with additional tests. However, binaurally balanced LDL and the Threshold-of-Hearing measurements for each frequency at these volume levels are difficult because they unnecessarily increase the patient's testing stress. For this reason binaurally balanced estimations of these values are typically better to reduce testing stress.

One method of estimating binaurally balanced left and right LDL values is to first calculate the average of the left and right monaural LDL measurements. Next, the average of the nearest binaurally balanced measurements is calculated. Then, the difference between these 2 averages is calculated. Finally, the calculated differences are added to the nearest left and right binaurally balanced measurements to estimate the binaurally balanced left LDL and right LDL values.

One method of estimating binaurally balanced left and right Threshold-of-Hearing values is to first calculate the average of the left and right monaural Threshold-of-Hearing measurements. Next, the average of the nearest binaurally balanced measurements is calculated. Then, the difference between these 2 averages is determined. Finally, the difference is subtracted from the nearest left and right binaurally balanced measurements to estimate the binaurally balanced left and right Threshold-of-Hearing values.

The foregoing estimating methods were applied to the binaurally balanced measurement array example provided in above. The array modified by these estimates is shown in the following Table 2.

two points of data are best generated at a comfortable listening level of the patient and at a loud listening level (SPLs) although other levels may also be used. The additional data used according to the present invention, such as threshold-of-hearing levels and loudness discomfort levels can be derived according to the principles of the present invention or derived from other sources. For example, the threshold-of-hearing levels can be provided by an audiogram and the loudness-discomfort levels could be taken from government standards, e.g., NIOSH. Thus, a mere two points of data are needed to derive the gain compensation curve for each gain compression channel of a hearing aid. Depending on the configuration of the hearing aid, more or less data points may be required. For example, some hearing aids have a single channel. Thus, for each pair of hearing aids (right and left), only two sets of points (one set for the left and one set for the right) are needed to define all gain compensation curves. Other hearing aids have more gain compression channels. Thus, for hearing aids having eight channels, sixteen sets of data points would be necessary to derive the gain compensation curves (eight sets for the left and eight sets for the right) and program the hearing aids.

In order to reduce the total test time, variations of the testing order may be employed. Those of skill in the art will appreciate that many variations and modifications of the testing sequence described herein can be made without departing from the spirit and scope of the present invention. One such variation is to perform the Binaurally Balanced Measurement Array immediately after the patient completes the Full Spectrum Loudness Discomfort Level Routine and the Full Spectrum Threshold-of-Hearing Routine and then conclude testing with the Binaurally Balanced Equal-loudness Contour Routine, but without the final steps for binaural balancing of the contour as these measurements might be interpolated from the measurement array.

TABLE 2

| Binaurally Balanced Measurement Array: | SPL Left Ear | SPL Right Ear | Estimated Value or Measurement Level: |
|---|---|---|---|
| Estimated Values: | | | |
| Loudness Discomfort Level: | 92.6 dB | 87.8 dB | Average $SPL_{CLL}$ + 12.4 dB |
| Binaural Balance: Binaurally Balanced | 87.2 dB | 82.4 dB | Average $SPL_{CLL}$ + 7 dB |
| Equal-loudness Level: | 79.3 dB | 76.3 dB | Average $SPL_{CLL}$ |
| Binaural Balance: | 69.2 dB | 66.4 dB | Average $SPL_{CLL}$ − 10 dB |
| Binaural Balance: | 58.5 dB | 57.1 dB | Average $SPL_{CLL}$ − 20 dB |
| Binaural Balance: Estimated Values: | 48.2 dB | 47.4 dB | Average $SPL_{CLL}$ − 30 dB |
| Threshold-of-Hearinq Level: | 38.3 dB | 37.5 dB | Average $SPL_{CLL}$ − 39.9 dB |

Figure 15:
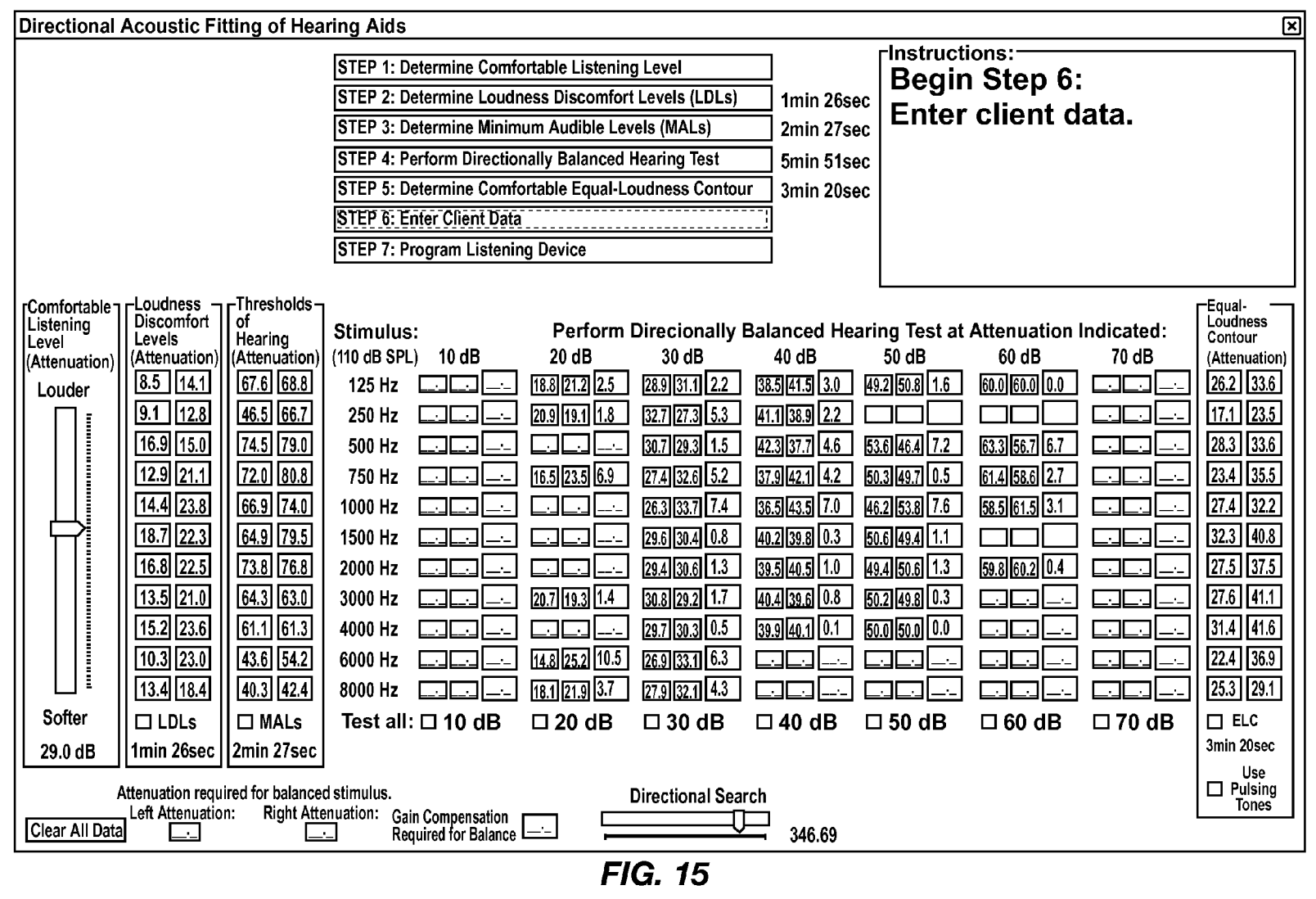

Accordingly, the methods for deriving gain compensation curves according to the present invention require only two points of data for each frequency in order to define a straight line in log-log space (dB SPL Input vs. dB SPL Output). The As shown in FIG. 15, the test results for a patient with moderate hearing loss using this variation are provided on a computer display screen through the software of the present invention. In this case the Binaurally Balanced Measurement Array was performed for fixed stimulus levels between the patient's LDLs and threshold-of-hearing measurements. The fixed stimulus levels were spaced every 10 dB. The entire test resulted in 145 measurements and was completed in 14 minutes. The test subject in this case allowed the software to determine directional affirmation by waiting for the last 3 one second SPL readings for each ear to differ by no more than 0.4 dB (using the methods identified in FIGS. 6 and 7). The patient may also click the mouse button to indicate that he/she has determined that the stimulus is exactly balanced for both ears. If the patient decides to click the mouse to record his/her localization determination, the entire test period is significantly reduced. Approximately 300 seconds (5 minutes) are saved. Most patients can complete the entire test in 9 to 10 minutes if they click the mouse to indicate the stimulus is exactly balanced. It should also be noted that the number of measurements made is arbitrary. More tests may be made using different frequency intervals and different SPL spacing. The number of tests may also be reduced by the patient's available dynamic hearing range.

The data collected using the procedures of the present invention as illustrated and described herein are employed to modify the gain compensation curves of hearing aids for proper hearing aid fitting. Many factors are considered for gain compensation programming strategies. For example, gradually developing noise-induced hearing loss (NIHL) occurs from the combination of sound intensity and duration of exposure. The safe exposure limit is up to 85 dB(A) over an 8 hours period.

For every 3 dB above this level, the exposure time is halved. Thus, the "safe" exposure at 91 dB(A) is only 2 hours (National Institute for Occupational Safety and Health, 1998). The U.S. Department of Labor's Occupational Safety and Health Administration (OSHA) states that exposure to 90 dB(A) of noise, known as an exposure action value, for more than eight hours per day can result in permanent hearing loss (Occupational Health and Safety Administration [OSHA], 2002). "A"-weighting (dB(A)) is defined in the International standard IEC 61672:2003 and relates to the measurement of sound pressure level, as opposed to actual sound pressure.

Hearing aids are often prescribed for NIHL. As hearing loss progresses, prescriptive gain increases. Poor gain compensation programming strategies may result in unintentionally accelerating NIHL by exceeding generally accepted safe exposure levels. Hearing aid programming must include the net exposure level by time integration to actively limit the total daily exposure. Without including this consideration into gain compensation programming, the audiologist and/or the hearing aid manufacturer may be responsible and liable for NIHL acceleration.

Gain and dynamic range management are other important factors that need to be considered when programming for gain compensation. The SPL for a very quiet room is 20 to 30 dB. The SPL for normal talking at 1 meter is 40 to 60 dB. The SPL for screaming and shouting is 75 to 85 dB. Hearing aid users are most interested in assistance with speech communication especially in the presence of noise. Thus, for a majority of programming situations, gain compensation should be maximized for input SPLs between 30 and 65 phons.

The dynamic hearing range for an individual can be defined as the SPLs between the LDL and Threshold-of-Hearing for each frequency. The dynamic range for a hearing impaired person is sometimes smaller than the dynamic range for the individual with normal hearing. The comfortable listening level for the hearing impaired is most often numerically closer to the LDL than it is to the Threshold-of-Hearing when compared to the person with normal hearing due to recruitment.

For purposes of Stenger and recruitment compensation, one possible gain compensation programming strategy output maps the patient's binaurally balanced equal-loudness contour at the comfortable listening level to an input map consisting of a targeted phon equal-loudness curve such as the 60 phon curve defined in the International Standard: ISO 226:2003 (an International Standard which specifies combinations of sound pressure levels and frequencies of pure continuous tones which are perceived as equally loud by human listeners). Note that the targeted phon curve may be derived as an interpolation of values between existing phon curves. The comparison of input to output SPLs will suggest an overall gain required for each of the individual hearing aid frequency channels to achieve a comfortable listening level which is then modified and optimized for the patient's available dynamic range and coordinated for correlated binaural directional perception across all frequency channels in order to create a family of channel specific gain compensation curves. The significant expansion of data made available by these data collection strategies suggest refinement to all current gain compensation programming strategies known in the art to now include coordinated and correlated binaural direction perception. Whereas patient specific data starvation has limited previous gain compensation programming strategies, it is now anticipated that many new strategies will also be suggested by the availability of this additional patient specific data.

The data collection strategies and measurement techniques according to the present invention require accurate sound level equipment calibration for the hearing aid fitted individual to achieve precise sound localization. As stated by a leading manufacturer of digital signal processors (DSPs) for hearing aids (Sound Design Technologies, Burlington, Ontario, Canada in Informational Note 17810-6): "When measuring the microphones and zero-bias receivers, it is important to remember that a typical broadband microphone's sensitivity has ±3 dB tolerance. The sensitivity of Ski Slope or Step microphones has ±4 dB tolerance. As well, the sensitivity of a passive telecoil has ±2 dB tolerance and an amplified telecoil has ±3 dB tolerance. Also, a typical zero-bias receiver's sensitivity can vary by as much as ±3 dB."

The digital-to-analog and analog-to-digital converters included with typical DSP devices may add errors of ±1 dB or more. An accumulation of calibration errors between testing, measurement, and implementation of the individualized gain compensation curves will defeat a portion of the precise sound localization made possible by this technology. Ideally, the accumulation of the component device errors should be known to within a few tenths of a dB and included in the gain compensation programming.

Optimally or optionally, the fitting process could be performed by the hearing aid itself for stimulus and measurement. A direct USB interface between a personal computer and the hearing aid itself could be used. With this approach, each individual hearing aid microphone and/or receiver could be precisely measured in a factory laboratory environment prior to shipping and programming. An azimuth sensor for head azimuth detection and measurement for instinctual sound direction affirmation in the fitting process could be included in the hearing aid electronics. The sensor might only be powered during the fitting process. A tiny interface module might also be used which contain signal translators necessary for data communication with the hearing aids and the USB.

This interface module might also contain the azimuth sensor and even sound card functionality to interface with the hearing aid receiver and DSP.

By using the actual hearing aid receivers, digital-to-analog converters, and the physically fitted configuration, the actual directional acoustic fitting described herein may be used to compensate for variations of some of these individual devices by including their errors in the gain compensation programming measurements.

The hearing aids themselves can be used to measure microphone sensitivity and analog-to-digital conversion accuracy. If all of hearing aids microphones for both hearing aids are tested simultaneously in the same anechoic test chamber using a single acoustic coupler, the relative compensation required may be more accurately determined.

Alternatively, the audiologist may be required to use a specific personal computer, sound card, and headphone set for the measurement and fitting process which has been factory calibrated by the hearing aid manufacturer. Another approach might be to require the use of self-calibrating equipment which might also be factory supplied and USB interfaced to the personal computer.

A hybrid approach could also be used where the some of the testing was performed with the headphones and PC and the hearing aids themselves performing another portion of the test. Still another hybrid approach might be to perform identical tests with both the hearing aids and the PC/Headphones such as the threshold of hearing test where the measurements are then compared and thereby calibrated with appropriate compensations. Upon review of the calibration strategies of the present invention, other calibration strategies may be apparent to those skilled in the art.

Some digital hearing aid designs use microphone pre-amplifiers prior to analog-to-digital (A/D) conversion. Some pre-amplifiers employ automatic gain control (AGC), especially in situations where the signal processing dynamic range of the A/D converter is insufficient for the entire SPL range of the microphone. Although newer 20 and 24 bit A/D converters may not require pre-amplification with AGC, older A/D converter designs continue to be used in some cases. The use of AGC before A/D conversion can diminish or negate the benefits of binaurally balanced localization. Some designers have chosen to use high-level AGC limiters to limit distortion at high SPLs. In many cases, the use of AGC limiters would not substantially reduce the benefits of binaurally balanced localization. If the A/D converter has at least 6 dB more electronic dynamic range than the microphone, AGC may be completely avoided.

Directional perception below 1000 Hz is dominated by the perception of the slight timing variations (also known as "interaural time differences"). Research has shown that the ear can detect a time (delay) difference as slight as 30 microseconds. Referencing a typical adult head, the maximum time lag for sound generated at one side of the head is around 0.6 milliseconds.

The SA3400 *Preliminary Data Sheet* for the Wolverine™ Open Platform DSP System for Ultra Low Power Audio Processing from Sound Design Technologies™ (Ontario, Canada) advertises low-delay anti-aliasing filters enabling sub 1 millisecond processing latency. TWO PI Signal Processing Applications GMBH (Vienna, Austria) advertises that their SWIFT-DYNAMIC RANGE COMPRESSION algorithm features a processing delay (group delay) of 2.5 milliseconds which virtually eliminates reverberation effects. Hearing aid manufacturers use system-on-chip (SoC), components, and hearing aid algorithm suites from a variety of sources. The processing delays sited in just these 2 examples are up to 100 times greater than detectible interaural time difference perception. Such delays create a convincing argument for binaural fitting of hearing aids to achieve the benefits of binaurally coordinated sound localization even in situations of monaural hearing loss. In addition, it is extremely important that coordinated interaural time differences are maintained for binaural directional perception and that they are correlated with the directional perception of interaural amplitude differences. Fortunately, interaural time differences for 2 hearing aids fitted to a single individual may be pre-measured at the factory across a spectrum of gain and programming configurations. According to the present invention, programming for gain compensation also includes the necessary individual frequency channel delay adjustments for each hearing aid to coordinate and correlate both interaural time differences and interaural amplitude differences to produce directional perception sameness.

The present invention thus provides dynamic derivation and programming of the individual gain compensation curves of a hearing aid during the audiometrical protocol described herein. Programming of the gain compensation curves of the hearing aid only at the conclusion of the protocol is also anticipated. Such programming of the hearing aid at intervals during the protocol is also anticipated.

Although the binaural fitting of a pair of hearing aids are described herein, it is anticipated that the individual may only require a single hearing aid for one ear. The methods of deriving gain compensation curves in fitting hearing aids utilizing head azimuth measurement and directional fitting provided herein are still applicable. For such cases, it is still important to realize that the protocol creates left and right data pairs for coordinated directional perception and that a frequency/amplitude data points for the left side are still tied to corresponding data points for the right side. For the individual requiring only a single hearing aid, the hearing compensation curves for the single hearing aid will be dependent on independent data points for the ear that does not require a hearing aid.

It should also be noted that the term "hearing aid(s)" as used throughout the specification and claims in describing the present invention is the term commonly used by audiologist, other ear care professionals, and/or governing regulatory agencies. It is intended, however, that other terms such as "personal sound amplifiers" that may from time-to-time be used to describe or distinguish such devices that may or may not be under controlled distribution by governing regulatory agencies or fitted by trained ear care professionals, but that are similar in nature to hearing aids are intended to be within the scope of the term "hearing aid(s)". Thus, devices distinguished by such terms as "personal sound amplifiers" are not to be so distinguished for the purposes and intents of this invention. Personal sound amplifiers and other such similar descriptions shall be considered synonymous and equivalent to hearing aids for the purposes of this invention.

It should also be noted that the term "threshold" and "threshold of hearing" as used throughout the specification and claims in describing the present invention are the terms commonly used by audiologist, other ear care professionals, and/or governing regulatory agencies. It is intended, however, that other terms such as "minimum audible level" that may from time-to-time be used to describe or distinguish such similar measurements that are similar in nature are intended to be within the scope of the term "threshold" and "threshold of hearing". Thus, such terms are not to be so distinguished for the purposes and intents of this invention. Minimum audible level and other such similar descriptions shall be considered synonymous and equivalent to threshold and threshold of hearing for the purposes of this invention.

It should also be noted that the term "gain compensation curves" and "curves" as used throughout the specification and claims in describing the present invention are the terms commonly used by engineers, programmers and technicians. It is intended, however, that such terms not exclude "linear" and "linear gain compensation" such as might be viewed on a log-log plot of input versus output sound pressure levels. Thus, such terms as curve and linear are not to be so distinguished for the purposes and intents of this invention.

It would be apparent to those skilled in the art that some other method of deriving gain compensation curves or other modifications could be employed in a similar manner for directional testing and gain compensation curve programming without departing from the inventive concepts herein. Thus, while there have been described various embodiments of the present invention, those skilled in the art will recognize that other and further changes and modifications may be made thereto without department from the spirit of the invention, and it is intended to claim all such changes and modifications that fall within the true scope of the invention. It is also understood that, as used herein and in the appended claims, the singular forms "a," "an," and "the" include plural reference, unless the context clearly dictates otherwise.

Unless defined otherwise, all technical and scientific terms used herein have the same meanings as commonly understood by one of ordinary skill in the art to which this invention belongs. While various methods and structures of the present invention are described herein, any methods or structures similar or equivalent to those described herein may be used in the practice or testing of the present invention. All references cited herein are incorporated by reference in their entirety and for all purposes. In addition, while the foregoing advantages of the present invention are manifested in the illustrated embodiments of the invention, a variety of changes can be made to the configuration, design and construction of the invention to achieve those advantages including combinations of components of the various embodiments. Hence, reference herein to specific details of the structure and function of the present invention is by way of example only and not by way of limitation.

What is claimed is:

1. A method of deriving individual gain compensation curves for hearing aid fitting, comprising:
    providing a hardware and software system that detects, measures and records head azimuth for sound direction affirmation by a patient;
    establishing thresholds-of-hearing levels of the patient comprising:
        providing a user interface coupled to the system for allowing user input during at least one hearing test;
        providing pulsing tones to the ears of the patient, with each frequency of the pulsing tones for each ear being individually swept with ever decreasing intensity;
        allowing the patient to use the user interface to indicate to the system when the pulsing tones are no longer heard; and
        recording the pulsing tone level for each ear of the patient when the patient uses the user interface to indicate to the system when the pulsing tones are no longer heard;
    providing a plurality of audio signals through a plurality of test sequences to the ears of the patient, wherein the plurality of test sequences comprise:
        establishing binaural balance for right and left ears of the patient comprising;
            measuring an equal-loudness level by providing a first tone with a first sound pressure level to one ear of the patient and a second tone with a second sound pressure level to the other ear of the patient and varying the first and second sound pressure levels according to azimuth head motion; and
            instructing the patient to turn their head until the first tone is perceived to be equal to or balanced with the second tone between both ears of the patient; and
        generating at least two data points for each ear corresponding to the measured equal-loudness level with each data point of the at least two data points taken at different SPLs.

2. The method of claim 1, further comprising establishing a comfortable listening level of the patient and adjusting an average sound pressure level for the plurality of test sequences to the right and left ears of the patient to the comfortable listening level.

3. The method of claim 2, wherein establishing the binaural balance further comprises setting the average of the first and second tones to an alternate comfort setting.

4. The method of claim 1, further comprising establishing a level louder than the comfortable listening level of the patient and adjusting an average sound pressure level for the plurality of test sequences to the right and left ears of the patient to the level louder than the comfortable listening level.

5. The method of claim 4, wherein establishing the binaural balance further comprises setting the average of the first and second tones to an alternate comfort setting.

6. The method of claim 1, further comprising alternating the tone between the left and right ears of the patient to reduce listening fatigue.

7. The method of claim 1, further comprising generating a binaural balanced measurement array of measured equal-loudness levels from the at least two data points that includes a binaurally balanced equal-loudness contour at a comfortable listening level of the patient.

8. The method of claim 7, wherein generating the binaural balanced measurement array further comprises limiting each of the different SPLs by a measured loudness discomfort level and a measured threshold of hearing level of the patient.

9. The method of claim 1, further comprising excluding the tones from the binaurally balanced measurements if the tone is outside the patient's range of hearing perception for either ear.

10. The method of claim 1, further comprising adjusting a speech volume for test taking instructions of the system to the established comfortable listening level.

11. The method of claim 1, wherein measurements and data collected during the plurality of test sequences are left and right coordinated so that any minor independent adjustments made for gain compensation curves for one ear are dependently reflected in adjustments for gain compensation curves made for the other ear.

12. A method of deriving individual gain compensation curves for hearing aid fitting, comprising:
    providing a hardware and software system that detects, measures and records head azimuth for sound direction affirmation by a patient;
    establishing loudness discomfort levels of the patient comprising:
        providing a user interface coupled to the system for allowing user input during at least one hearing test; and providing continuous tones to the ears of the patient, with each frequency of the continuous tones for each ear being individually swept with ever increasing intensity;

allowing the patient to use the user interface to indicate to the system when the volume becomes uncomfortably loud; and recording the pulsing tone level for each ear of the patient when the patient uses the user interface to indicate to the system when the pulsing tones are no longer heard;

providing a plurality of audio signals through a plurality of test sequences to the ears of the patient, wherein the plurality of test sequences comprise:

establishing binaural balance for right and left ears of the patient comprising;

measuring an equal-loudness level by providing a first tone with a first sound pressure level to one ear of the patient and a second tone with a second sound pressure level to the other ear of the patient and varying the first and second sound pressure levels according to azimuth head motion; and instructing the patient to turn their head until the first tone is perceived to be equal to or balanced with the second tone between both ears of the patient; and generating at least two data points for each ear corresponding to the measured equal-loudness level with each data point of the at least two data points taken at different SPLs.

13. The method of claim 12, further comprising establishing a comfortable listening level of the patient and adjusting an average sound pressure level for the plurality of test sequences to the right and left ears of the patient to the comfortable listening level.

14. The method of claim 12, further comprising establishing a level louder than the comfortable listening level of the patient and adjusting an average sound pressure level for the plurality of test sequences to the right and left ears of the patient to the level louder than the comfortable listening level.

15. The method of claim 12, further comprising alternating the first and second tones between the left and right ears of the patient to reduce listening fatigue.

16. The method of claim 12, wherein establishing the binaural balance further comprises setting the average of the first and second tones to an alternate comfort setting.

17. The method of claim 12, wherein establishing the binaural balance further comprises setting the average of the first and second tones to an alternate comfort setting.

18. The method of claim 12, further comprising generating a binaural balanced measurement array of measured equal-loudness levels from the at least two data points that includes a binaurally balanced equal-loudness contour at a comfortable listening level of the patient.

19. The method of claim 18, wherein generating the binaural balanced measurement array further comprises limiting each of the different SPLs by a measured loudness discomfort level and a measured threshold of hearing level of the patient.

20. A method of deriving individual gain compensation curves for hearing aid fitting, comprising:

providing a hardware and software system that detects, measures and records head azimuth for sound direction affirmation by a patient;

establishing binaural balance for right and left ears of the patient comprising;

measuring the equal-loudness levels by providing a first tone to one ear of the patient and a second tone at a different frequency to the other ear of the patient with the SPL of the ear receiving the first tone being fixed and varying the SPL of the second tone according to azimuth head motion;

instructing the patient to turn their head until the sound is perceived to be balanced in both ears; and recording the SPL of the second tone when the sound is perceived to be balanced in both ears; and providing a plurality of audio signals through a plurality of test sequences to the ears of the patient, wherein the plurality of test sequences comprise:

establishing binaural balance for right and left ears of the patient comprising;

measuring an equal-loudness level by providing a first tone with a first sound pressure level to one ear of the patient and a second tone with a second sound pressure level to the other ear of the patient and varying the first and second sound pressure levels according to azimuth head motion; and instructing the patient to turn their head until the first tone is perceived to be equal to or balanced with the second tone between both ears of the patient; and generating at least two data points for each ear corresponding to the measured equal-loudness level with each data point of the at least two data points taken at different SPLs.

21. The method of claim 20, further comprising establishing a comfortable listening level of the patient and adjusting an average sound pressure level for the plurality of test sequences to the right and left ears of the patient to the comfortable listening level.

22. The method of claim 20, further comprising establishing a level louder than the comfortable listening level of the patient and adjusting an average sound pressure level for the plurality of test sequences to the right and left ears of the patient to the level louder than the comfortable listening level.

23. The method of claim 20, further comprising alternating the first and second tones between the left and right ears of the patient to reduce listening fatigue.

24. The method of claim 20, wherein establishing the binaural balance further comprises setting the average of the first and second tones to an alternate comfort setting.

25. The method of claim 20, further comprising generating a binaural balanced measurement array of measured equal-loudness levels from the at least two data points that includes a binaurally balanced equal-loudness contour at a comfortable listening level of the patient.

26. The method of claim 25, wherein generating the binaural balanced measurement array further comprises limiting each of the different SPLs by a measured loudness discomfort level and a measured threshold of hearing level of the patient.

27. The method of claim 20, further comprising excluding the tones from the binaurally balanced measurements if the tone is outside the patient's range of hearing perception for either ear.

28. The method of claim 20, further comprising adjusting a speech volume for test taking instructions of the system to the established comfortable listening level.

29. The method of claim 20, wherein measurements and data collected during the plurality of test sequences are left and right coordinated so that any minor independent adjustments made for gain compensation curves for one ear are dependently reflected in adjustments for gain compensation curves made for the other ear.

30. A method of deriving individual gain compensation curves for hearing aid fitting, comprising:

providing a hardware and software system that detects, measures and records head azimuth for sound direction affirmation by a patient;

providing a plurality of audio signals through a plurality of test sequences to the ears of the patient, wherein the plurality of test sequences comprise:

establishing binaural balance for right and left ears of the patient comprising;

measuring an equal-loudness level by providing a first tone with a first sound pressure level to one ear of the patient and a second tone with a second sound pressure level to the other ear of the patient and varying the first and second sound pressure levels according to azimuth head motion; and instructing the patient to turn their head until the first tone is perceived to be equal to or balanced with the second tone between both ears of the patient;

generating at least two data points for each ear corresponding to the measured equal-loudness level with each data point of the at least two data points taken at different SPLs;

providing at least one practice session that includes localization practice comprising instructing the patient to practice precise localization with a tone by turning the head of the patient until the tone is balanced in both ears or until the patient perceives that the he/she is facing a source of the tone and monitoring the head movement of the patient during the localization practice; and continuing the localization practice until the average azimuth position and corresponding SPL for each ear for the last one second of collected data is approximately equal to the two preceding one second averages.

31. The method of claim 30, further comprising establishing a comfortable listening level of the patient and adjusting an average sound pressure level for the plurality of test sequences to the right and left ears of the patient to the comfortable listening level.

32. The method of claim 30, further comprising establishing a level louder than the comfortable listening level of the patient and adjusting an average sound pressure level for the plurality of test sequences to the right and left ears of the patient to the level louder than the comfortable listening level.

33. The method of claim 30, further comprising alternating the first and second tones between the left and right ears of the patient to reduce listening fatigue.

34. The method of claim 30, wherein establishing the binaural balance further comprises setting the average of the first and second tones to an alternate comfort setting.

35. The method of claim 30, further comprising generating a binaural balanced array measurement of measured equal-loudness levels from the at least two data points that includes a binaurally balanced equal-loudness contour at a comfortable listening level of the patient.

36. The method of claim 35, wherein generating the binaural balanced measurement array further comprises limiting each of the different SPLs by a measured loudness discomfort level and a measured threshold of hearing level of the patient.

37. The method of claim 30, further comprising excluding the tones from the binaurally balanced measurements if the tone is outside the patient's range of hearing perception for either ear.

38. The method of claim 30, further comprising adjusting a speech volume for test taking instructions of the system to the established comfortable listening level.

39. The method of claim 30, wherein measurements and data collected during the plurality of test sequences are left and right coordinated so that any minor independent adjustments made for gain compensation curves for one ear are dependently reflected in adjustments for gain compensation curves made for the other ear.

* * * * *